United States Patent
Norton et al.

(10) Patent No.: US 8,921,387 B2
(45) Date of Patent: Dec. 30, 2014

(54) INJECTABLE FLOWABLE COMPOSITION COMPRISING BUPRENORPHINE

(75) Inventors: Richard L. Norton, Fort Collins, CO (US); Andrew Watkins, Fort Collins, CO (US); Mingxing Zhou, Fort Collins, CO (US)

(73) Assignee: RB Pharmaceuticals Limited, Slough, Berkshire (GB)

(*) Notice: Subject to any disclaimer, the term of this patent is extended or adjusted under 35 U.S.C. 154(b) by 214 days.

(21) Appl. No.: 13/703,013

(22) PCT Filed: Jun. 6, 2011

(86) PCT No.: PCT/GB2011/051057
§ 371 (c)(1),
(2), (4) Date: Jan. 27, 2013

(87) PCT Pub. No.: WO2011/154724
PCT Pub. Date: Dec. 15, 2011

(65) Prior Publication Data
US 2013/0210853 A1    Aug. 15, 2013

(30) Foreign Application Priority Data
Jun. 8, 2010  (GB) .................................. 1009549.5

(51) Int. Cl.
*A01N 43/42*     (2006.01)
*A61K 31/44*     (2006.01)
*A61K 9/00*      (2006.01)
*A61K 31/485*    (2006.01)
*A61K 47/34*     (2006.01)

(52) U.S. Cl.
CPC ............. *A61K 9/0002* (2013.01); *A61K 9/0024* (2013.01); *A61K 31/485* (2013.01); *A61K 47/34* (2013.01)

USPC ......................................................... 514/282

(58) Field of Classification Search
USPC ......................................................... 514/282
See application file for complete search history.

(56) References Cited

U.S. PATENT DOCUMENTS

2003/0211157 A1    11/2003 Simon
2004/0033250 A1     2/2004 Patel

FOREIGN PATENT DOCUMENTS

| WO | 2004043432 A2 | 5/2004 | |
|----|---------------|--------|--|
| WO | 2009091737 A2 | 7/2009 | |
| WO | WO2009091737  * | 7/2009 | ............. A61L 27/17 |

OTHER PUBLICATIONS

Graves et al, In Vitro Dissolution Method for Evaluation of Buprenorphine in Situ Gel Formulation: A Technical Note, 2007, AAPS PharmSciTech, 8(3), pp. E1-E4.*

(Continued)

*Primary Examiner* — Trevor Love
(74) *Attorney, Agent, or Firm* — Troutman Sanders, LLP; Ryan A. Schneider; Troy S. Kleckley

(57) ABSTRACT

The present invention is directed to a buprenorphine sustained release delivery system capable of delivering buprenorphine, a metabolite, or a prodrug thereof for a duration of about 14 days to about 3 months. The buprenorphine sustained release delivery system includes a flowable composition and a solid implant for the sustained release of buprenorphine, a metabolite, or a prodrug thereof. The implant is produced from the flowable composition. The buprenorphine sustained release delivery system provides in situ 1-month and 3-month release profiles characterized by an exceptionally high bioavailability and minimal risk of permanent tissue damage and typically no risk of muscle necrosis.

7 Claims, 3 Drawing Sheets

Buprenorphine release after subcutaneous injection of buprenorphine hydrochloride ATRIGEL™ formulations in rats

(56) References Cited

OTHER PUBLICATIONS

International Search Report mailed May 23, 2012 for priority application PCT/GB2011/051057.
Search Report dated Oct. 4, 2010 for priority application GB1009549.5.
Graves Richard A et al: "In vitro dissolution method for evaluation of buprenorphine in situ gel formulation: a technical note.", AAPS Pharmscitech 2007 LNKD-Pubmed:17915812, vol. 8, No. 3, 2007.
International Preliminary Report on Patentability issued Dec. 10, 2012 in priority application PCT/GB2011/051057.

* cited by examiner

Figure 1. Buprenorphine release after subcutaneous injection of buprenorphine hydrochloride ATRIGEL™ formulations in rats
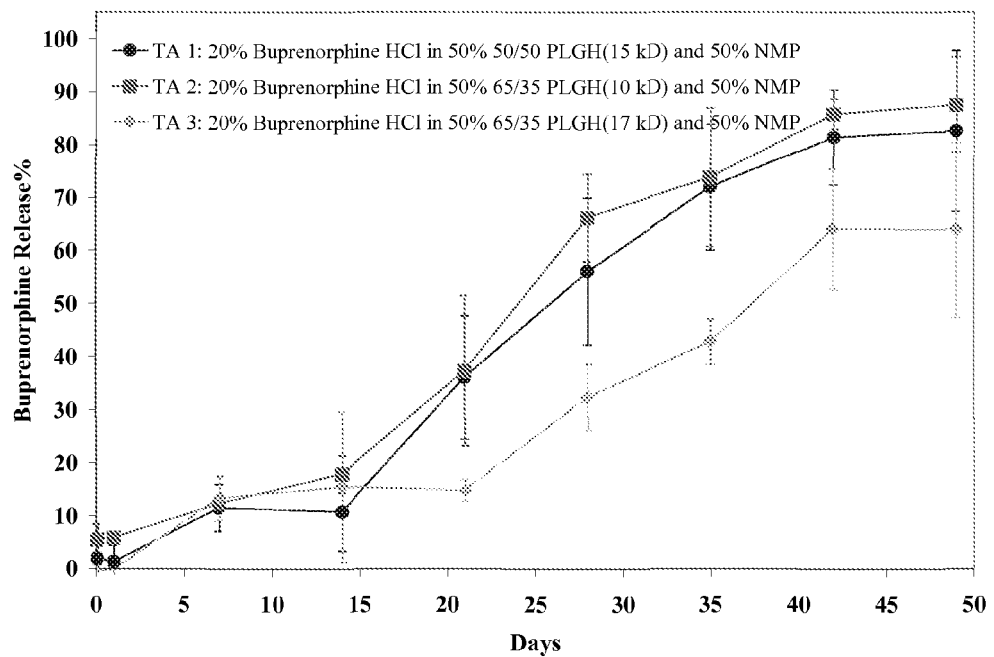
Figure 2. Buprenorphine release after suncutaneous injection of buprenorphine free base ATRIGEL™ formulations in rats
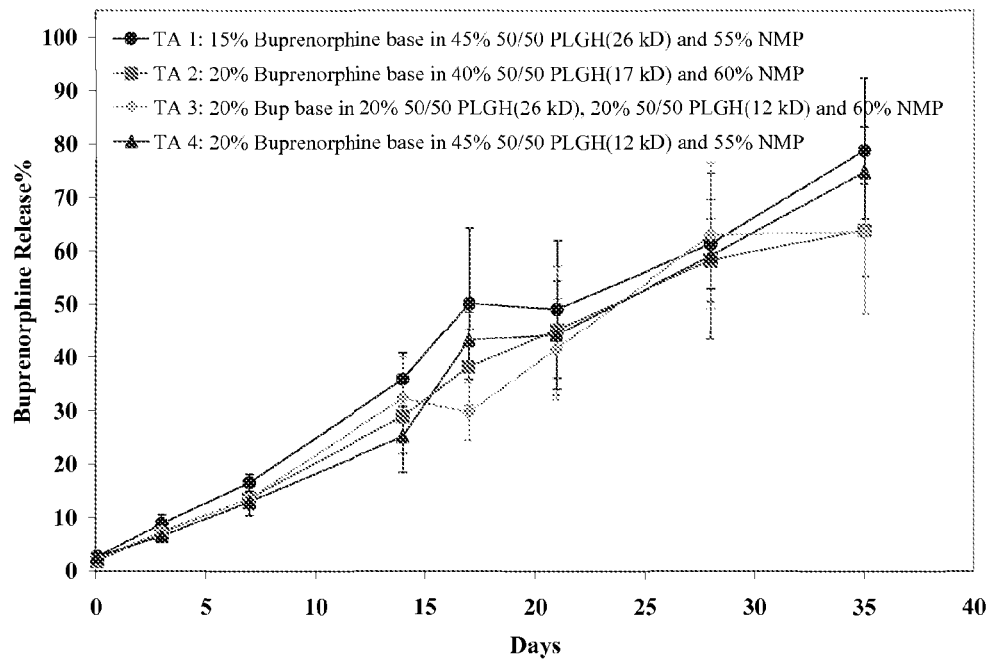

Figure 3. Plasma buprenorphine levels after subcutaneous injection of buprenorphine free base ATRIGEL™ formulations in rats
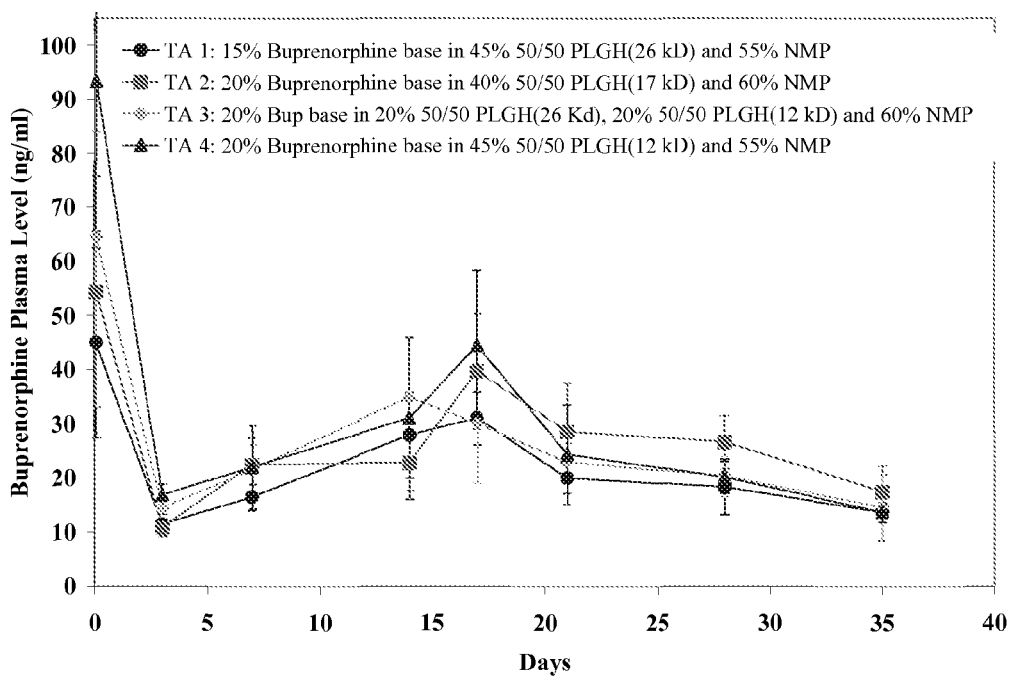
Figure 4. Mean plasma buprenorphine levels after subcutaneous injection of two buprenorphine hydrochloride ATRIGEL™ formulations in Beagles
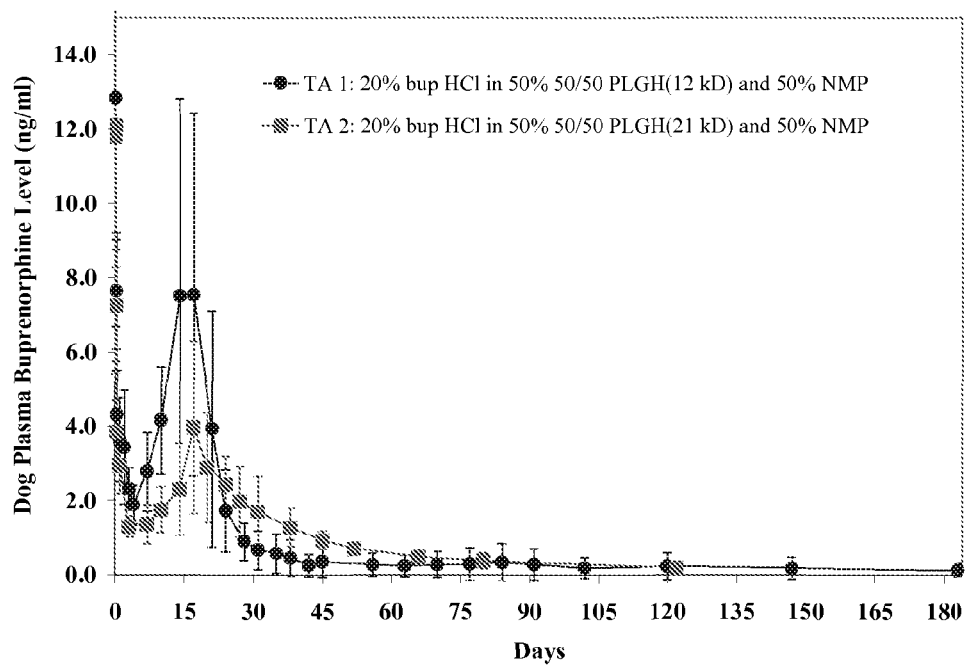

Figure 5. Mean plasma buprenorphine levels after subcutaneous injection of four buprenorphine free base ATRIGEL™ formulations in Beagles
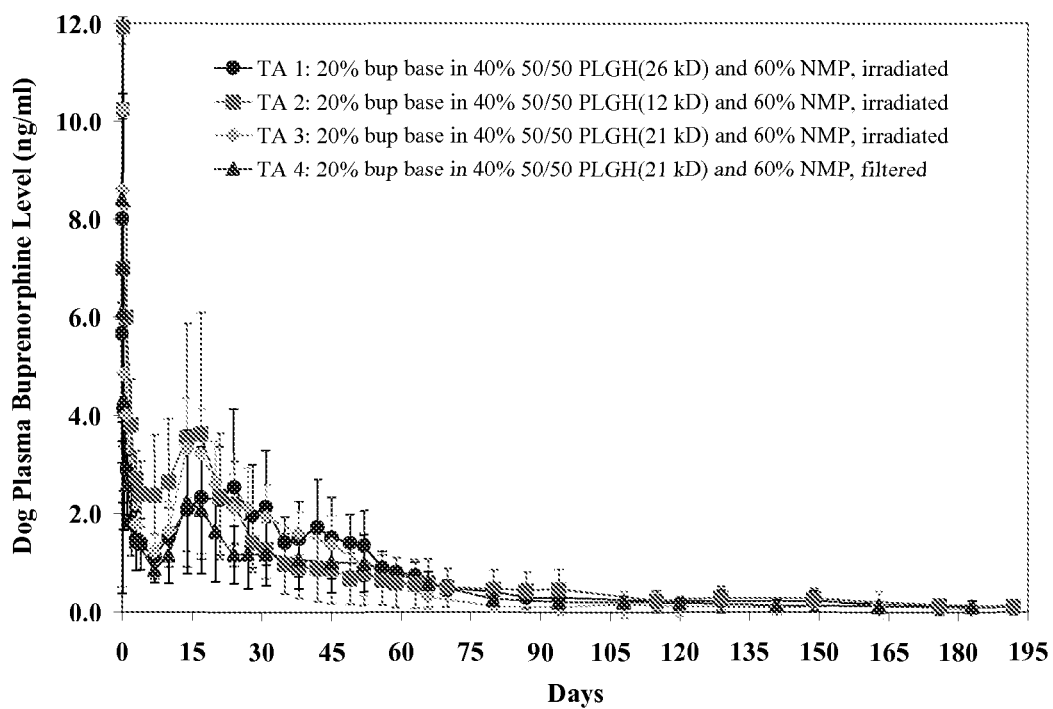

INJECTABLE FLOWABLE COMPOSITION COMPRISING BUPRENORPHINE

CROSS-REFERENCE TO RELATED APPLICATIONS

This application is a US National Stage of International Application No. PCT/GB2011/051057, filed 6 Jun. 2011, which claims the benefit of GB 1009549.5, filed 8 Jun. 2010, both herein fully incorporated by reference.

FIELD OF THE INVENTION

This disclosure relates to a buprenorphine sustained release delivery system for treatment of conditions ameliorated by buprenorphine compounds. The sustained release delivery system includes a flowable composition containing buprenorphine, a metabolite, or a prodrug thereof and an implant containing buprenorphine, a metabolite, or a prodrug thereof.

BACKGROUND OF THE INVENTION

Buprenorphine (also known as (2S)-2-[(−)-(5R,6R,7R,14S)-9α-cyclo-propyl-methyl-4,5-epoxy-6,14-ethano-3-hydroxy-6-methoxymorphinan-7-yl]-3,3-di-methylbutan-2-ol and marketed under the trade names SUBUTEX™ and SUBOXONE™ for relief of opioid addiction.

The chemical structure of buprenorphine is shown in formula (1).

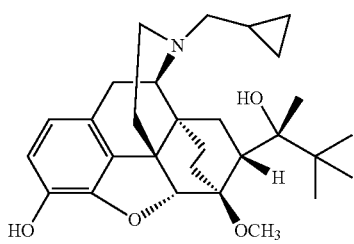

Formula (1)

Buprenorphine is most often used to treat symptoms arising from opioid addiction and for the long term relief of pain. Currently, the commercial products are SUBUTEX™ and SUBOXONE™ marketed by RB Pharma Inc. These products are in a tablet formulation and are intended to deliver therapeutic levels of buprenorphine for short periods of time of up to several hours and are typically taken either buccally or sub-lungually. However, the patient is required to supplement this dose at regular intervals, and there are often issues with diversion in patients with an opioid dependence problem. There is a need therefore for a longer term, non-divertible method of administering buprenorphine which delivers a constant and effective dose of the active to the patient over a period of up to 30 days, and which does not result in an unwanted accumulation of residual active in the patient's metabolism.

Various sustained release methods are employed in the pharmaceutical industry, for example, systems such as solid, biodegradable rods, or nondegradable reservoirs. These, however, typically require surgical implantation and furthermore, for the nondegradable delivery systems, a second surgical procedure is required to remove the empty reservoir.

There is a continuing need to develop products providing increased bioavailability of buprenorphine. In particular, there is a need to develop sustained release formulations of buprenorphine that do not suffer from low bioavailability, poor release kinetics, injection site toxicity, relatively large volume injections, and inconveniently short duration of release

SUMMARY OF THE INVENTION

The present invention is directed to a buprenorphine sustained release delivery system capable of delivering buprenorphine, a metabolite, or a prodrug thereof for a duration of about 14 days to about 3 months. The buprenorphine sustained release delivery system includes a flowable composition and a solid implant for the sustained release of buprenorphine, a metabolite, or a prodrug thereof. The implant is produced from the flowable composition. The buprenorphine sustained release delivery system provides in situ 1-month and 3-month release profiles characterized by an exceptionally high bioavailability and minimal risk of permanent tissue damage and typically no risk of muscle necrosis.

In one embodiment, a buprenorphine sustained release delivery system is provided. This delivery system includes a flowable composition and a controlled, sustained release implant. The flowable composition according to this embodiment comprises a biodegradable thermoplastic polymer, a biocompatible, polar organic liquid, and buprenorphine, a metabolite, or a prodrug thereof. The flowable composition may be transformed into the implant by contact with water, body fluid, or other aqueous medium. In one embodiment, the flowable composition is injected into the body whereupon it transforms in situ into athe solid implant.

According to a first embodiment of the present invention, therefore, there is provided an injectable flowable composition comprising:
(a) at least one biodegradable thermoplastic polymer which is at least substantially insoluble in body fluid;
(b) a biocompatible polar aprotic organic liquid which comprises an amide, an ester, a carbonate, a lactam, an ether, a sulfonyl, or any combination thereof; which has a solubility in aqueous medium or body fluid ranging from insoluble to completely soluble in all proportions; and,
(c) 1 wt % to 10 wt % of buprenorphine, a metabolite, or a prodrug thereof; wherein the composition is transformed in situ into a solid implant by contact with water, body fluid or other aqueous medium.

The thermoplastic polymer of the flowable composition and implant is at least substantially insoluble in an aqueous medium or body fluid, or typically completely insoluble in those media. The thermoplastic polymer may be a homopolymer, a copolymer, or a terpolymer of repeating monomeric units linked by such groups as ester groups, anhydride groups, carbonate groups, amide groups, urethane groups, urea groups, ether groups, esteramide groups, acetal groups, ketal groups, orthocarbonate groups, and any other organic functional group that can be hydrolyzed by enzymatic or hydrolytic reaction (i.e., is biodegradable by this hydrolytic action). The thermoplastic polymer may be a polyester that may be composed of units of about one or more hydroxycarboxylic acid residues, or diol and dicarboxylic acid residues, wherein the distribution of differing residues may be random, block, paired, or sequential. The polyester may be a combination of about one or more diols and about one or more dicarboxylic acids. The hydroxy carboxylic acid or acids may also be in the form of dimers.

When the biodegradable thermoplastic polymer is a polyester, the polyesters include, for example, a polylactide, a polyglycolide, a polycaprolactone, a copolymer thereof, a terpolymer thereof, or any combination thereof, optionally incorporating a third mono-alcohol or polyol component. More preferably, the biodegradable thermoplastic polyester is a polylactide, a polyglycolide, a copolymer thereof, a terpolymer thereof, or a combination thereof, optionally incorporating a third mono-alcohol or polyol component. Preferably the polyester is a 50/50, 55/45, 60/40, 65/35, 70/30, 75/25, 80/20, 85/15, 90/10, or 95/5 poly(DL-lactide-co-glycolide) having a carboxy terminal group, or is a 50/50, 55/45, 60/40, 65/35, 70/30, 75/25, 80/20, 85/15, 90/10, or 95/5 poly(DL-lactide-co-glycolide) without a carboxy terminal group. More preferably, the suitable biodegradable thermoplastic polyester is about 50/50 poly(lactide-co-glycolide) (hereinafter PLG) having a carboxy terminal group or is a 75/25 or a 85/15 PLG with a carboxy terminal group or such a PLG formulated with about one or more mono-alcohol or polyol units. When a mono-alcohol or polyol is incorporated into the polyester, the mono-alcohol or polyol constitutes a third covalent component of the polymer chain. When a mono-alcohol is incorporated, the carboxy terminus of the polyester is esterified with the mono-alcohol. When a polyol is incorporated, it chain extends and optionally branches the polyester. The polyol functions as a polyester polymerization point with the polyester chains extending from multiple hydroxyl moieties of the polyol, and those hydroxyl moieties are esterified by a carboxyl group of the polyester chain. For an embodiment employing a diol, the polyester is linear with polyester chains extending from both esterified hydroxy groups. For an embodiment employing a triol or higher polyol, the polyester may be linear or may be branched with polyester chains extending from the esterified hydroxy groups. Suitable polyols include, for example, aliphatic and aromatic diols, saccharides such as glucose, lactose, maltose, sorbitol, triols such as glycerol, fatty alcohols, and the like, tetraols, pentaols, hexaols, and the like.

The biodegradable thermoplastic polymer can be present in any suitable amount, provided the biodegradable thermoplastic polymer is at least substantially insoluble in aqueous medium or body fluid. Preferably the biodegradable thermoplastic polyester is present in about 5 wt. % to about 95 wt. % of the flowable composition, or is present in about 15 wt. % to about 70 wt. % of the flowable composition, or is present in about 25 wt. % to about 50 wt. % of the flowable composition.

Preferably, the biodegradable thermoplastic polymer has an average molecular weight of about 5,000 Daltons (Da) to about 40,000 Daltons, or more preferably about 10,000 Daltons to about 20,000 Daltons.

The flowable composition also includes a biocompatible, polar organic liquid. The biocompatible polar liquid can be an amide, an ester, a carbonate, an ether, a sulfonyl, or any other organic compound that is liquid at ambient temperature and is polar. The organic liquid may be very slightly soluble to completely soluble in all proportions in body fluid. While the organic liquid generally should have similar solubility profiles in aqueous medium and body fluid, body fluid is typically more lipophilic than aqueous medium. Consequently, some organic liquids that are insoluble in aqueous medium should be at least slightly soluble in body fluid. These examples of organic liquid are included within the definition of organic liquids.

Preferably, the organic liquid comprises N-methyl-2-pyrrolidone, 2-pyrrolidone, N,N-dimethylformamide, dimethyl sulfoxide, propylene carbonate, caprolactam, triacetin, or any combination thereof. More preferably, the organic liquid is N-methyl-2-pyrrolidone. Preferably, the polar organic liquid is present in about 10 wt. % to about 90 wt. % of the composition or is present in about 30 wt. % to about 70 wt. % of the composition The buprenorphine, a metabolite, or a prodrug thereof is present in about 1 wt % to about 30 wt % of the flowable composition; preferably between 5 wt % and 25 wt %; more preferably between 8 wt % and 22 wt %.

In one embodiment, the buprenorphine, a metabolite, or a prodrug thereof in the flowable composition may be in the neutral or free base form. In a further embodiment, the buprenorphine, a metabolite, or a prodrug thereof in the flowable composition may be in the form of a salt and the salt gegenion may be derived from a pharmaceutically acceptable organic or inorganic acid, or the gegenion may be a polycarboxylic acid.

In a further preference, the weight ratio of the buprenorphine, a metabolite, or a prodrug thereof to the biodegradable thermoplastic polymer(s) is between 0.001:1 and 1.5:1.

The flowable composition is formulated as an injectable delivery system. The flowable composition preferably has a volume of about 0.10 mL to about 2.0 mL or preferably about 0.20 mL to about 1.0 mL. The injectable composition is preferably formulated for administration about once per month, about once per three months, or about once per four months, to about once per six months. Preferably, the flowable composition is a liquid or a gel composition, suitable for injection into a patient. The flowable composition may have the property of production of minimal tissue necrosis when injected subcutaneously.

Excipients, release modifiers, plasticizers, pore forming agents, gelation liquids, non-active extenders, and other ingredients may also be included within the buprenorphine sustained release delivery system. Upon administration of the flowable composition, some of these additional ingredients, such as gelation liquids and release modifiers should remain with the implant, while others, such as pore forming agents should separately disperse and/or diffuse along with the organic liquid.

In one embodiment, a method is provided for forming a flowable composition for use as a controlled release implant. The method includes mixing, in any order, a biodegradable thermoplastic polymer, a biocompatible polar aprotic liquid, and buprenorphine, a metabolite, or a prodrug thereof. The biodegradable thermoplastic polymer may be at least substantially insoluble in aqueous medium or body fluid. These ingredients, their properties, and preferred amounts are as disclosed above. The mixing is performed for a sufficient period of time effective to form the flowable composition for use as a controlled release implant. Preferably, the biocompatible thermoplastic polymer and the biocompatible polar aprotic organic liquid are mixed together to form a mixture and the mixture is combined with the buprenorphine, a metabolite, or a prodrug thereof to form the flowable composition. Preferably, the flowable composition is a solution or dispersion, especially preferably a solution, of the buprenorphine, a metabolite, or a prodrug thereof and biodegradable thermoplastic polymer in the organic liquid. The flowable composition preferably includes an effective amount of a biodegradable thermoplastic polymer, an effective amount of a biocompatible polar aprotic organic liquid, and an effective amount of buprenorphine, a metabolite, or a prodrug thereof. These ingredients, the preferred ingredients, their properties, and preferred amounts are as disclosed above.

In one embodiment, a biodegradable implant formed in situ, in a patient is provided, by the steps including: injecting a flowable composition including a biodegradable thermoplastic polymer that is at least substantially insoluble in body fluid, a biocompatible polar aprotic organic liquid; and buprenorphine, a metabolite, or a prodrug thereof into the body of the patient, and allowing the biocompatible polar aprotic liquid to dissipate to produce a solid or gel biodegradable implant. The flowable composition includes an effective amount of the biodegradable thermoplastic polymer, an effective amount of the biocompatible polar aprotic liquid, and an effective amount of buprenorphine, a metabolite, or a prodrug thereof and the solid implant releases an effective amount of buprenorphine, a metabolite, or a prodrug thereof over time as the solid implant biodegrades in the patient and optionally the patient is a human.

In one embodiment, a method is provided of forming a biodegradable implant in situ, in a living patient. The method includes injecting the flowable composition including a biodegradable thermoplastic polymer that is at least substantially insoluble in body fluid, a biocompatible polar aprotic organic liquid, and buprenorphine, a metabolite, or a prodrug thereof within the body of a patient and allowing the biocompatible polar aprotic organic liquid to dissipate to produce a solid biodegradable implant. Preferably, the biodegradable solid implant releases an effective amount of buprenorphine, a metabolite, or a prodrug thereof by diffusion, erosion, or a combination of diffusion and erosion as the solid implant biodegrades in the patient.

In one embodiment, a method is provided of treating or preventing mammalian diseases that are ameliorated, cured, or prevented by buprenorphine, a metabolite, or a prodrug thereof. The method includes administering, to a patient (preferably a human patient) in need of such treatment or prevention, an effective amount of a flowable composition including a biodegradable thermoplastic polymer that is at least substantially insoluble in body fluid, a biocompatible polar aprotic organic liquid, and buprenorphine, a metabolite, or a prodrug thereof.

In a further embodiment, a kit is provided. In a preferred form of this embodiment, the kit includes a first container and a second container. The first container includes a composition of the biodegradable thermoplastic polymer and the biocompatible polar aprotic organic liquid. The biodegradable thermoplastic polymer may be at least substantially insoluble in aqueous medium or body fluid. The second container includes buprenorphine, a metabolite, or a prodrug thereof. These ingredients, their properties, and preferred amounts are as disclosed above. Preferably, the first container is a syringe and the second container is a syringe. The kit can preferably include, for example, instructions. Preferably, the first container can be connected to the second container. More preferably, the first container and the second container are each configured to be directly connected to each other.

In a further form of this embodiment, the kit comprises a single syringe comprising a composition comprising a biodegradable thermoplastic polymer that is at least substantially insoluble in a body fluid, a biocompatible polar aprotic liquid and buprenorphine, a metabolite, or a prodrug thereof.

In a further embodiment, a solid implant is provided. The solid implant is composed of at least the biocompatible thermoplastic polymer and buprenorphine, a metabolite, or a prodrug thereof and is substantially insoluble in body fluid. The biodegradable thermoplastic polymer may be at least substantially insoluble in aqueous medium or body fluid. While buprenorphine, a metabolite, or a prodrug thereof itself has at least some solubility in body fluid, its isolation within the substantially insoluble implant allows for its slow, sustained release into the body.

The solid implant has a solid matrix or a solid microporous matrix. The matrix can be a core surrounded by a skin. The implant may be solid and microporous. When microporous, the core preferably contains pores of diameters from about 1 to about 1000 microns. When microporous, the skin preferably contains pores of smaller diameters than those of the core pores. In addition, the skin pores are preferably of a size such that the skin is functionally non-porous in comparison with the core. The solid implant can optionally include, for example, one or more biocompatible organic substances which may function as an excipient as described above, or which may function as a plasticizer, a sustained release profile modifier, emulsifier, and/or isolation carrier for buprenorphine, a metabolite, or a prodrug thereof. The biocompatible organic liquid may also serve as an organic substance of the implant and/or may provide an additional function such as a plasticizer, a modifier, an emulsifier, or an isolation carrier. There may be two or more organic liquids present in the flowable composition such that the primary organic liquid acts as a mixing, solubilizing, or dispersing agent, and the supplemental organic liquid or liquids provide additional functions within the flowable composition and the implant. Alternatively, there may be one organic liquid which at least may act as a mixing, solubilizing, or dispersing agent for the other components, and may provide additional functions as well. As second or additional components, additional kinds of biodegradable organic liquids typically are combined with the flowable composition and may remain with the implant as the administered flowable composition coagulates.

When serving as a plasticizer, the biocompatible organic substance provides such properties as flexibility, softness, moldability, and drug release variation to the implant. When serving as a modifier, the biocompatible organic substance also provides the property of buprenorphine release variation to the implant. Typically, the plasticizer increases the rate of buprenorphine, a metabolite, or a prodrug thereof release while the modifier slows the rate of buprenorphine, a metabolite, or a prodrug thereof release. Also, there can be structural overlap between these two kinds of organic substances functioning as plasticizers and rate modifiers.

When serving as an emulsifier, the biocompatible organic substance at least in part enables a uniform mixture of the buprenorphine, a metabolite, or a prodrug thereof within the flowable composition and within the implant. When serving as an isolation carrier, the biocompatible organic substance should function to encapsulate, isolate, or otherwise surround molecules or nanoparticles of the buprenorphine, a metabolite, or a prodrug thereof so as to prevent its burst at least in part, and to isolate the buprenorphine, a metabolite, or a prodrug thereof from degradation by other components of the flowable composition and implant.

The amount of biocompatible organic substance optionally remaining in the solid or gel implant is preferably minor, such as from about 0 wt. % (or an almost negligible amount) to about 20 wt. % of the composition. In addition, the amount of biocompatible organic substance optionally present in the solid or gel implant preferably decreases over time.

The solid implant may also include, for example, a biocompatible organic liquid that is very slightly soluble to completely soluble in all proportions in body fluid and at least partially dissolves at least a portion of the thermoplastic polyester, and optionally the amount of biocompatible organic liquid is less than about 5 wt. % of the total weight of the implant, and optionally the amount of biocompatible organic liquid decreases over time.

The solid implant may also include, for example, a core that contains pores of diameters from about 1 to about 1000 microns, and optionally the skin contains pores of smaller diameters than those of the core pores, and optionally the skin pores are of a size such that the skin is functionally nonporous in comparison with the core.

In one embodiment, a flowable composition having an initial limited burst followed by a substantially linear release profile, then a period of gradually slower release. Preferably, the linear release profile lasts for 28 days.

In one embodiment, a method is provided for treatment of a patient having a medical condition including administering to the patient an effective amount of buprenorphine, a metabolite, or a prodrug thereof in combination with an at least substantially water-insoluble biodegradable thermoplastic polymer and a biocompatible, polar, aprotic organic liquid, wherein the medical condition comprises opioid addiction and chronic pain. This method of treatment may include, for example, combination therapy with another known pharmaceutical compound designated for treatment of the malcondition.

Preferably the flowable composition is formulated for administration about once per month, or about once per three months, or about once per four months, or about once per six months.

In one embodiment, a method is provided for treating a patient having a medical condition comprising administering to the patient a flowable composition to provide a biodegradable implant comprising buprenorphine, a metabolite, or a prodrug thereof and a biodegradable polymer, wherein the implant releases delivers therapeutically effective dosage from about 0.1 to about 10 milligrams (mg) of buprenorphine, a metabolite, or a prodrug thereof per day, or preferably from about 1 to about 5 milligrams (mg) of buprenorphine, a metabolite, or a prodrug thereof per day. The therapeutically effective dosage of buprenorphine, a metabolite, or a prodrug thereof may be achieved within about five days after administration of the implant, or preferably, within about one day after administration of the implant. The therapeutically effective dosage of buprenorphine, a metabolite, or a prodrug thereof may be delivered for at least about 15 days after administration of the implant, or preferably for at least about 28 days after administration of the implant, or preferably for at least about 45 days after administration of the implant, or preferably for at least about 60 days after administration of the implant.

BRIEF DESCRIPTION OF THE DRAWINGS

FIG. 1 illustrates the 49 day release of buprenorphine from selected ATRIGEL™ formulations of buprenorphine hydrochloride subcutaneously injected in rats.

FIG. 2 illustrates the 35 day release of buprenorphine from selected ATRIGEL™ formulations of buprenorphine free base injected in rats.

FIG. 3 illustrates the 35 day release of buprenorphine from further selected ATRIGEL™ formulations of buprenorphine free base injected in rats.

FIG. 4 illustrates the 180 day plasma concentration of active buprenorphine in in dogs injected with an Atrigel/(buprenorphine hydrochloride) formulation.

FIG. 5 illustrates the 195 day release of buprenorphine from selected ATRIGEL™ formulations in dogs injected with an Atrigel/(buprenorphine free base) formulation.

DEFINITIONS

As used herein, the singular forms "a," "an," and "the" include plural reference unless the context clearly dictates otherwise. Thus, for example, a reference to "a formulation" includes a plurality of such formulations, so that a formulation of compound X includes formulations of compound X.

As used herein, the term "acceptable salts" refer to derivatives wherein the parent compound is modified by making acid or base salts thereof. Suitable acceptable salts include, but are not limited to, mineral or organic acid salts of basic residues such as amines; alkali or organic salts of acidic residues such as carboxylic acids; and the like. The acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Specifically, the acceptable salts can include, for example, those salts that naturally occur in vivo in a mammal.

As used herein, the term "biocompatible" means that the material, substance, compound, molecule, polymer, or system to which it applies should not cause severe toxicity, severe adverse biological reaction, or lethality in an animal to which it is administered at reasonable doses and rates.

As used herein, the term "biodegradable" means that the material, substance, compound, molecule, polymer, or system is cleaved, oxidized, hydrolyzed, or otherwise broken down by hydrolytic, enzymatic, or another mammalian biological process for metabolism to chemical units that can be assimilated or eliminated by the mammalian body.

As used herein, the term "bioerodable" means that the material, substance, compound, molecule, polymer, or system is biodegraded or mechanically removed by a mammalian biological process so that new surface is exposed.

As used herein, average molecular weight is the weight average molecular weight of a polymer as determined by gel permeation chromatography (also known as GPC or size exclusion chromatography (SEC)) using tetrahydrofuran (THF) as the solvent and using a molecular weight calibration curve using polystyrene standards.

As used herein, the term "therapeutically effective amount" is intended to include an amount of buprenorphine, a metabolite, or a prodrug thereof, a pharmaceutically acceptable salt thereof, a derivative thereof, or any combination of those useful to treat or prevent the underlying disorder or disease, or to treat the symptoms associated with the underlying disorder or disease in a host. Synergy, as described, for example, by Chou and Talalay, Adv. Enzyme Regul. 22, 27-55 (1984), occurs when the effect of buprenorphine, a metabolite, or a prodrug thereof, a pharmaceutically acceptable salt thereof, or a derivative thereof when administered in combination is greater than the additive effect of the buprenorphine, a metabolite, or a prodrug thereof, pharmaceutically acceptable salt thereof, or a derivative thereof when administered alone as a single agent. In general, a synergistic effect is most clearly demonstrated at suboptimal concentrations of the buprenorphine, a metabolite, or a prodrug thereof, a pharmaceutically acceptable salt thereof, or derivative thereof. Synergy can be in terms of lower cytotoxicity, increased activity, or some other beneficial effect of the combination compared with the individual components.

As used herein, the term "flowable" refers to the ability of the "flowable" composition to be transported under pressure into the body of a patient. For example, the flowable composition can have a low viscosity like water, and be injected with the use of a syringe, beneath the skin of a patient. The flowable composition can alternatively have a high viscosity as in a gel and can be placed into a patient through a high pressure transport device such as a high pressure syringe, cannula, needle, and the like. The ability of the composition to be injected into a patient should typically depend upon the viscosity of the composition. The composition should therefore have a suitable viscosity ranging from low like water to high like a gel, such that the composition can be forced through the transport device (e.g., syringe) into the body of a patient.

As used herein, the term "gel" refers to a substance having a gelatinous, jelly-like, or colloidal properties. See, e.g., CONCISE CHEMICAL AND TECHNICAL DICTIONARY, 4th Edition, Chemical Publishing Co., Inc., p. 567, New York, N.Y. (1986).

As used herein, the term "liquid" refers to a substance that undergoes continuous deformation under a shearing stress. See, e.g., CONCISE CHEMICAL AND TECHNICAL DICTIONARY, 4th Edition, Chemical Publishing Co., Inc., p. 707, New York, N.Y. (1986).

As used herein, the term "patient" refers to a warm-blooded animal, and preferably a mammal, such as, for example, a cat, dog, horse, cow, pig, mouse, rat, or primate, including a human. As used herein, the term "polymer" refers to a molecule of one or more repeating monomeric residue units covalently bonded together by one or more repeating chemical functional groups. The term includes all polymeric forms such as linear, branched, star, random, block, graft, and the like. It includes homopolymers formed from a single monomer, copolymer formed from two or more monomers, terpolymers formed from three or more polymers, and polymers formed from more than three monomers. Differing forms of a polymer may also have more than one repeating, covalently bonded functional group. The term may also refer to substantially linear polyesters, also referred to herein as "PLG copolymers," predominantly formed of monomeric lactate and glycolate hydroxyacids, or lactide and glycolide dimeric hydroxyacids, and include, for example, compositions referred to in the art as poly(lactate-glycolate), poly(lactate(co)glycolate), poly(lactide-glycolide), poly(lactide(co)glycolide), PLG, PLGH, and the like, with the understanding that additional moieties may be included, such as core/initiator groups (for example, diols, hydroxyacids, and the like), capping groups (for example, esters of terminal carboxyl groups, and the like) and other pendant groups or chain extension groups covalently linked to or within a polyester backbone, including groups that cross-link the substantially linear polyester molecular chains, without departing from the meaning assigned herein. PLG copolymers, as the term is used herein, includes molecular chains with terminal hydroxyl groups, terminal carboxyl groups (i.e., acid-terminated, sometimes termed PLGH) and terminal ester groups (i.e., capped).

As used herein, the term "polyester" refers to polymers containing monomeric repeats, at least in part, of the linking group: —OC(═O)— or —C(═O)O—.

As used herein, the terms "skin" and "core" of a skin and core matrix mean that a cross section of the matrix should present a discernable delineation between an outer surface and the inner portion of the matrix. The outer surface is the skin and the inner portion is the core. As used herein, the term "thermoplastic" as applied to a polymer means that the polymer repeatedly should melt upon heating and should solidify upon cooling. It signifies that no or a slight degree of cross-linking between polymer molecules is present. It is to be contrasted with the term "thermoset" which indicates that the polymer should set or substantially cross-link upon heating or upon application of a similar reactive process and should no longer undergo melt-solidification cycles upon heating and cooling.

As used herein, the terms "treating," "treat," or "treatment" includes (i) preventing a pathologic condition (e.g., schizophrenia) from occurring (e.g., prophylaxis); (ii) inhibiting the pathologic condition (e.g., schizophrenia) or arresting its development; and (iii) relieving the pathologic condition (e.g., relieving the symptoms associated with schizophrenia).

DESCRIPTION OF THE INVENTION

The present invention is directed to a buprenorphine sustained release delivery system. The sustained release delivery system includes a flowable composition and a solid implant. The delivery system provides an in situ sustained release of buprenorphine, a metabolite, or a prodrug thereof. The flowable composition accomplishes the sustained release through its use to produce the implant. The implant has a low implant volume and provides a long term delivery of buprenorphine, a metabolite, or a prodrug thereof. The flowable composition enables subcutaneous formation of the implant in situ and causes little or no tissue necrosis. The in situ implant provides therapeutic plasma buprenorphine, a metabolite, or a prodrug thereof levels immediately after injection and maintains steady-state plasma levels from four to six weeks.

Another advantage of one embodiment includes a simple manufacturing process and delivery system. For example, the buprenorphine, a metabolite, or a prodrug thereof is filled into a syringe, the syringe is sealed, and the entire drug substance syringe is terminally sterilized by gamma irradiation. The biodegradable polymer used is dissolved in N-methyl-2-pyrrolidinone and filled in a second syringe. The syringe is sealed and the delivery system is terminally sterilized by gamma irradiation. At the time of injection, the syringes are coupled through the luer-lock connection and the product is constituted by cycling the components between the two syringes. In this way, the drug is incorporated into the delivery system and very little is lost to the device.

The flowable composition is a combination of a biodegradable, at least substantially water-insoluble thermoplastic polymer, a biocompatible polar aprotic organic liquid and buprenorphine, a metabolite, or a prodrug thereof. The polar, aprotic organic liquid has a solubility in body fluid ranging from practically insoluble to completely soluble in all proportions. Preferably, the thermoplastic polymer is a thermoplastic polyester of about one or more hydroxycarboxylic acids or about one or more diols and dicarboxylic acids. Especially preferably, the thermoplastic polymer is a polyester of about one or more hydroxylcarboxyl dimers such as lactide, glycolide, dicaprolactone, and the like.

The specific and preferred biodegradable thermoplastic polymers and polar aprotic solvents; the concentrations of thermoplastic polymers, polar aprotic organic liquids, and buprenorphine, a metabolite, or a prodrug thereof; the molecular weights of the thermoplastic polymer; and the weight or mole ranges of components of the solid implant described herein are exemplary. They do not exclude other biodegradable thermoplastic polymers and polar aprotic organic liquids; other concentrations of thermoplastic polymers, polar aprotic liquids, and buprenorphine, a metabolite, or a prodrug thereof; other molecular weights of the thermoplastic polymer; and other components within the solid implant.

In one embodiment, a flowable composition suitable for use in providing a controlled sustained release implant is provided, a method for forming the flowable composition, a method for using the flowable composition, the biodegradable sustained release solid or gel implant that is formed from the flowable composition, a method of forming the biodegradable implant in situ, a method for treating disease through use of the biodegradable implant and a kit that includes the flowable composition. The flowable composition may preferably be used to provide a biodegradable or bioerodible microporous in situ formed implant in animals. The flowable composition is composed of a biodegradable thermoplastic polymer in combination with a biocompatible polar aprotic organic liquid and buprenorphine, a metabolite, or a prodrug thereof. The biodegradable thermoplastic polymer is substantially insoluble in aqueous medium and/or in body fluid, biocompatible, and biodegradable and/or bioerodible within the body of a patient. The flowable composition may be administered as a liquid or gel into tissue and forms an implant in situ. Alternatively, the implant may be formed ex vivo by combining the flowable composition with an aqueous medium. In this embodiment, the preformed implant may be surgically administered to the patient. In either embodiment, the thermoplastic polymer coagulates or solidifies to form the solid or gel implant upon the dissipation, dispersement, or leaching of the organic liquid from the flowable composition when the flowable composition contacts a body fluid, an aqueous medium, or water. The coagulation or solidification entangles and entraps the other components of the flowable composition such as buprenorphine, a metabolite, or a prodrug thereof excipients, organic substances, and the like, so that they become dispersed within the gelled or solidified implant matrix. The flowable composition is biocompatible and the polymer matrix of the implant does not cause substantial tissue irritation or necrosis at the implant site. The implant delivers a sustained level of buprenorphine, a metabolite, or a prodrug thereof to the patient. Preferably, the flowable composition can be a liquid or a gel, suitable for injection in a patient (e.g., human).

One embodiment surprisingly improves the bioavailability of a sustained release formulation of buprenorphine, a metabolite, or a prodrug thereof. In addition, one embodiment provides: (a) relatively low volume injections; (b) improved local tissue tolerance at the injection site; (c) an opportunity to use a subcutaneous injection rather than an intramuscular injection; and (d) less frequent injections compared to other products.

By comparison to formulations derived from other sustained release drug delivery technologies, the buprenorphine sustained release delivery system should provide: (a) superior release kinetics with minimal burst; (b) increased duration of drug release with less frequent injections; (c) markedly improved bioavailability; (d) improved local tissue tolerance due to a small injection volume, and (e) the ability to use of a subcutaneous injection rather than intramuscular injection. Taken together, these features make a highly beneficial buprenorphine sustained release delivery system.

Biodegradable Thermoplastic Polymer

The flowable composition is produced by combining a solid, biodegradable thermoplastic polymer, buprenorphine, a metabolite, or a prodrug thereof and a biocompatible polar aprotic organic liquid. The flowable composition can be administered by a syringe and needle to a patient in need of treatment. Any suitable biodegradable thermoplastic polymer can be employed, provided that the biodegradable thermoplastic polymer is at least substantially insoluble in body fluid.

The biocompatible, biodegradable, thermoplastic polymer can be made from a variety of monomers which form polymer chains or monomeric units joined together by linking groups. The thermoplastic polymer is composed of a polymer chain or backbone containing monomeric units joined by such linking groups as ester, amide, urethane, anhydride, carbonate, urea, esteramide, acetal, ketal, or orthocarbonate groups as well as any other organic functional group that can be hydrolyzed by enzymatic or hydrolytic reaction (i.e., is biodegradable by this hydrolytic action). The thermoplastic polymer is typically formed by reaction of starting monomers containing the reactant groups that should form the backbone linking groups. For example, alcohols and carboxylic acids should form ester linking groups. Isocyanates and amines or alcohols should respectively form urea or urethane linking groups.

Any aliphatic, aromatic, or arylalkyl starting monomer having the specified functional groups can be used to make the thermoplastic polymers, provided that the polymers and their degradation products are biocompatible. The monomer or monomers used in forming the thermoplastic polymer may be of a single or multiple identity. The resultant thermoplastic polymer should be a homopolymer formed from one monomer, or one set of monomers such as when a diol and diacid are used, or a copolymer, terpolymer, or multi-polymer formed from two or more, or three or more, or more than three monomers or sets of monomers. The biocompatiblity specifications of such starting monomers are known in the art. The thermoplastic polymers are substantially insoluble in aqueous media and body fluids, preferably completely insoluble in such media and fluids. They are also capable of dissolving or dispersing in selected organic liquids having a water solubility ranging from completely soluble in all proportions to water insoluble. The thermoplastic polymers also are biocompatible.

When used in the flowable composition, the thermoplastic polymer in combination with the organic liquid provides a viscosity of the flowable composition that varies from low viscosity, similar to that of water, to a high viscosity, similar to that of a paste, depending on the molecular weight and concentration of the thermoplastic polymer. Typically, the polymeric composition includes about 5 wt. % to about 95 wt. % of the flowable composition, preferably present in about 15 wt. % to about 70 wt. % of the flowable composition or more preferably is present in about 25 wt. % to about 50 wt. % of the flowable composition.

In one embodiment, the biodegradable, biocompatible thermoplastic polymer can be a linear polymer, it can be a branched polymer, or it can be a combination thereof. Any option is available according to one embodiment. To provide a branched thermoplastic polymer, some fraction of one of the starting monomers may be at least trifunctional, and preferably multifunctional. This multifunctional character provides at least some branching of the resulting polymer chain. For example, when the polymer chosen contains ester linking groups along its polymer backbone, the starting monomers normally should be hydroxycarboxylic acids, cyclic dimers of hydroxycarboxylic acids, cyclic trimers of hydroxycarboxylic acids, diols, or dicarboxylic acids. Thus, to provide a branched thermoplastic polymer, some fraction of a starting monomer that is at least multifunctional, such as a triol or a tricarboxylic acid is included within the combination of monomers being polymerized to form the thermoplastic polymer. In addition, the polymers may incorporate more than one multifunctional unit per polymer molecule, and typically many multifunctional units depending on the stoichiometry of the polymerization reaction. The polymers may also optionally incorporate at least about one multifunctional unit per polymer molecule. A so-called star or branched polymer is formed when about one multifunctional unit is incorporated in a polymer molecule. The preferred thermoplastic polyester may be formed from such monomers as hydroxycarboxylic acids or dimers thereof. Alternatively, a thermoplastic polyester may be formed from a dicarboxylic acid and a diol. A branching monomer such as a dihydroxycarboxylic acid would be included with the first kind of starting monomer, or a triol and/or a tricarboxylic acid would be included with the second kind of starting monomer if a branched polyester were desired. Similarly, a triol, tetraol, pentaol, or hexaol such as sorbitol or glucose can be included with the first kind of starting monomer if a branched or star polyester were desired. The same rationale would apply to polyamides. A triamine and/or triacid would be included with starting monomers of a diamine and dicarboxylic acid. An amino dicarboxylic acid, diamino carboxylic acid, or a triamine would be included with the second kind of starting monomer, amino acid. Any aliphatic, aromatic, or arylalkyl starting monomer having the specified functional groups can be used to make the branched thermoplastic polymers, provided that the polymers and their degradation products are biocompatible. The biocompatiblity specifications of such starting monomers are known in the art.

The monomers used to make the biocompatible thermoplastic polymers should produce polymers or copolymers that are thermoplastic, biocompatible, and biodegradable. Suitable thermoplastic, biocompatible, biodegradable polymers suitable for use as the biocompatible thermoplastic branched polymers include, for example, polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), and copolymers, terpolymers, combinations, or mixtures of the above materials. Suitable examples of such biocompatible, biodegradable, thermoplastic polymers are disclosed, e.g., in U.S. Pat. Nos. 4,938,763, 5,278,201, 5,324,519, 5,702,716, 5,744,153, 5,990,194, 6,461,631, and 6,565,874.

The polymer composition can also include, for example, polymer blends of the polymers with other biocompatible polymers, so long as they do not interfere undesirably with the biodegradable characteristics of the composition. Blends of the polymer with such other polymers may offer even greater flexibility in designing the precise release profile desired for targeted drug delivery or the precise rate of biodegradability desired for implants.

The preferred biocompatible thermoplastic polymers or copolymers are those which have a lower degree of crystallization and are more hydrophobic. These polymers and copolymers are more soluble in the biocompatible organic liquids than highly crystalline polymers such as polyglycolide, which has a high degree of hydrogen-bonding. Preferred materials with the desired solubility parameters are polylactides, polycaprolactones, and copolymers of these with glycolide so as to provide more amorphous regions to enhance solubility. Generally, the biocompatible, biodegradable thermoplastic polymer is substantially soluble in the organic liquid so that solutions, dispersions, or mixtures up to about 50-60 wt. % solids can be made. Preferably, the polymers are typically completely soluble in the organic liquid so that solutions, dispersions, or mixtures up to about 85-98 wt. % solids can be made. The polymers also are at least substantially insoluble in water so that less than about 0.1 g of polymer per mL of water should dissolve or disperse in water. Preferably, the polymers are typically completely insoluble in water so that less than about 0.001 g of polymer per mL of water should dissolve or disperse in water. At this preferred level, the flowable composition with a completely water miscible organic liquid should almost immediately transform to the solid implant.

Optionally, the delivery system may also contain a combination of a non-polymeric material and an amount of a thermoplastic polymer. The combination of non-polymeric material and thermoplastic polymer may be adjusted and designed to provide a more coherent buprenorphine sustained release delivery system. Non-polymeric materials useful are those that are biocompatible, substantially insoluble in water and body fluids, and biodegradable and/or bioerodible within the body of an animal. The non-polymeric material is capable of being at least partially solubilized in an organic liquid. In the flowable composition containing some organic liquid or other additive, the non-polymeric materials are also capable of coagulating or solidifying to form a solid or gel implant upon the dissipation, dispersement or leaching of the organic liquid component from the flowable composition upon contact of the flowable composition with a body fluid. The matrix of all embodiments of the implant including a non-polymeric material should have a consistency ranging from gelatinous to impressionable and moldable, to a hard, dense solid.

Non-polymeric materials that can be used in the delivery system generally include, for example, any having the foregoing characteristics. Suitable useful non-polymeric materials include, for example, sterols such as cholesterol, stigmasterol, beta-sistosterol, and estradiol; cholestery esters such as cholesteryl stearate, Ci8-C36 mono-, di-, and tricylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl tridocosanoate, glyceryl trimyristate, glyceryl tridecenoate, glyceryl tristearate, and mixtures thereof; sucrose fatty acid esters such as sucrose distearate and sucrose palmitate; sorbitan fatty acid esters such as sorbitan monostearate, sorbitan monopalmitate, and sorbitan tristearate; Ci6-Ci8 fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include, for example, cholesterol, glyceryl monostearate, glyceryl tristearate, stearic acid, stearic anhydride, glyceryl monooleate, glyceryl monolinoleate, and acetylated monoglycerides. The polymeric and non-polymeric materials may be selected and/or combined to control the rate of biodegradation, bioerosion, and/or bioabsorption within the implant site. Generally, the implant matrix should breakdown over a period from about 1 week to about 12 months, preferably over a period of about 1 week to about 4 months.

Thermoplastic Polymer Molecular Weight

The molecular weight of the polymer can affect the rate of buprenorphine, a metabolite, or a prodrug thereof release from the implant. Under these conditions, as the molecular weight of the polymer increases, the rate of buprenorphine, a metabolite, or a prodrug thereof release from the system decreases. This phenomenon can be advantageously used in the formulation of systems for the controlled release of buprenorphine, a metabolite, or a prodrug thereof. For faster release of buprenorphine, a metabolite, or a prodrug thereof, low molecular weight polymers can be chosen to provide the desired release rate. For release of buprenorphine, a metabolite, or a prodrug thereof over a relatively long period of time, a higher polymer molecular weight can be chosen. Accordingly, a buprenorphine sustained release delivery system can be produced with an optimum polymer molecular weight range for the release of buprenorphine, a metabolite, or a prodrug thereof over a selected length of time. The molecular weight of a polymer can be varied by any of a variety of methods. The choice of method is typically determined by the type of polymer composition. For example, if a thermoplastic polyester is used that is biodegradable by hydrolysis, the molecular weight can be varied by controlled hydrolysis, such as in a steam autoclave. Typically, the degree of polymerization can be controlled, for example, by varying the number and type of reactive groups and the reaction times.

The control of molecular weight and/or inherent viscosity of the thermoplastic polymer is a factor involved in the formation and performance of the implant. In general, thermoplastic polymers with higher molecular weight and higher inherent viscosity should provide an implant with a slower degradation rate and therefore a longer duration. Changes and fluxuations of the molecular weight of the thermoplastic polymer following the compounding of the delivery system should result in the formation of an implant that shows a degradation rate and duration substantially different from the degradation rate and duration desired or predicted.

The useful thermoplastic polymers may have average molecular weights ranging from about 1 kiloDalton (kDa) to about 100 kDa. Preferably, the biodegradable thermoplastic polymer has an average molecular weight of about 5,000 Daltons (Da) to about 40,000 Daltons, or more preferably about 10,000 Daltons to about 20,000 Daltons.

The molecular weight may also be indicated by the inherent viscosity (abbreviated as "IV.", units are in deciliters/gram). Generally, the inherent viscosity of the thermoplastic polymer is a measure of its molecular weight and degradation time (e.g., a thermoplastic polymer with a high inherent viscosity has a higher molecular weight and longer degradation time). Preferably, the thermoplastic polymer has a molecular weight, as shown by the inherent viscosity, from about 0.05 dL/g to about 0.5 dL/g (as measured in chloroform), more preferably from about 0.10 dL/g to about 0.30 dL/g.

Characteristics of Preferred Polyester

The preferred thermoplastic biodegradable polymer of the flowable composition is a polyester. Generally, the polyester may be composed of units of about one or more hydroxycarboxylic acid residues wherein the distribution of differing units may be random, block, paired, or sequential. Alternatively, the polyester may be composed of units of about one or more diols and about one or more dicarboxylic acids. The distribution should depend upon the starting materials used to synthesize the polyester and upon the process for synthesis. An example of a polyester composed of differing paired units distributed in block or sequential fashion is a poly(lactide-co-glycolide). An example of a polyester composed of differing unpaired units distributed in random fashion is poly(lactic acid-co-glycolic acid). Suitable biodegradable thermoplastic polyesters include, for example, polylactides, polyglycolides, polycaprolactones, copolymers thereof, terpolymers thereof, and any combinations thereof. Preferably, the suitable biodegradable thermoplastic polyester is a polylactide, a polyglycolide, a copolymer thereof, a terpolymer thereof, or a combination thereof.

The terminal groups of the poly(DL-lactide-co-glycolide) can either be hydroxyl, carboxyl, or ester depending upon the method of polymerization.

Polycondensation of lactic or glycolic acid should provide a polymer with terminal hydroxyl and carboxyl groups. Ring-opening polymerization of the cyclic lactide or glycolide monomers with water, lactic acid, or glycolic acid should provide polymers with these same terminal groups. However, ring-opening of the cyclic monomers with a mono functional alcohol such as methanol, ethanol, or 1-dodecanol should provide a polymer with about one hydroxyl group and about one ester terminal group. Ring-opening polymerization of the cyclic monomers with a polyol such as glucose, 1,6-hexanediol, or polyethylene glycol should provide a polymer with hydroxyl terminal groups. Such a polymerization of dimers of hydroxylcarboxylic acids and a polyol is a chain extension of the polymer. The polyol acts as a central condensation point with the polymer chain growing from the hydroxyl groups incorporated as ester moieties of the polymer. The polyol may be a diol, triol, tetraol, pentaol, or hexaol of about 2 to about 30 carbons in length. Examples include saccharides, reduced saccharides such as sorbitol, diols such as hexane-1,6-diol, triols such as glycerol or reduced fatty acids, and similar polyols.

Generally, the polyesters copolymerized with alcohols or polyols should provide longer duration implants.

The type, molecular weight, and amount of the preferred biodegradable thermoplastic polyester present in the flowable composition should typically depend upon the desired properties of the controlled sustained release implant. For example, the type, molecular weight, and amount of biodegradable thermoplastic polyester can influence the length of time in which the buprenorphine, a metabolite, or a prodrug thereof is released from the controlled sustained release implant. Specifically, in one embodiment, the composition can be used to formulate a one month sustained release delivery system of buprenorphine, a metabolite, or a prodrug thereof. In such an embodiment, the biodegradable thermoplastic polyester can be a 50/50, 55/45, 75/25, 85/15, 90/10, or 95/5 poly(DL-lactide-co-glycolide) having a carboxy terminal group, preferably a 50/50 poly(DL-lactide-co-glycolide) having a carboxy terminal group; can be present in about 20 wt. % to about 70 wt. % of the composition; and can have an average molecular weight of about 5,000 Daltons to about 40,000 Daltons, or preferably about 10,000 Daltons to about 20,000 Daltons.

In one embodiment, the flowable composition can be formulated to provide a sustained release delivery system of buprenorphine, a metabolite, or a prodrug thereof. In such an embodiment, the biodegradable thermoplastic polyester can be a 50/50, 55/45, 75/25, poly(DL-lactide-co-glycolide) with a carboxy terminal group; preferably be a 50/50 poly(DL-lactide-co-glycolide) with a carboxy terminal group; can be present in about 20 wt. % to about 50 wt. % of the composition; and can have an average molecular weight of about 5,000 Daltons to about 40,000 Daltons, or preferably about 10,000 Daltons to about 20,000 Daltons Polar Aprotic Organic Solvent Organic liquids suitable for use in the flowable composition are biocompatible and display a range of solubilities in aqueous medium, body fluid, or water. That range includes complete insolubility at all concentrations upon initial contact, to complete solubility at all concentrations upon initial contact between the organic liquid and the aqueous medium, body fluid, or water.

While the solubility or insolubility of the organic liquid in water can be used as a solubility guide, its water solubility or insolubility in body fluid typically should vary from its solubility or insolubility in water. Relative to water, body fluid contains physiologic salts, lipids, proteins, and the like, and should have a differing solvating ability for organic liquids. This phenomenon is similar to the classic "salting out" characteristic displayed by saline relative to water. Body fluid displays similar variability relative to water but in contrast to a "salting out" factor, body fluid typically has a higher solvating ability for most organic liquids than water. This higher ability is due in part to the greater lipophilic character of body fluid relative to water, and also in part to the dynamic character of body fluid. In a living organism, body fluid is not static but rather moves throughout the organism. In addition, body fluid is purged or cleansed by tissues of the organism so that body fluid contents are removed. As a result, body fluid in living tissue should remove, solvate, or dissipate organic liquids that are utterly insoluble in water.

Pursuant to the foregoing understanding of the solubility differences among water, aqueous media, and body fluid, the organic liquid may be completely insoluble to completely soluble in water when the two are initially combined. Preferably the organic liquid is at least slightly soluble, more preferably moderately soluble, especially more preferably highly soluble, and most preferably soluble at all concentrations in water. The corresponding solubilities of the organic liquids in aqueous media and body fluid should tend to track the trends indicated by the water solubilities. In body fluid, the solubilities of the organic liquids should tend to be higher than those in water. When an organic liquid that is insoluble to slightly soluble in body fluid is used in any of the embodiments of the sustained release delivery system, it should allow water to permeate into the implanted delivery system over a period of time ranging from seconds to weeks or months. This process may decrease or increase the delivery rate of the buprenorphine, a metabolite, or a prodrug thereof and in the case of the flowable composition, it should affect the rate of coagulation or solidification. When an organic liquid that is moderately soluble to very soluble in body fluid is used in any of the embodiments of the delivery system, it should diffuse into body fluid over a period of minutes to days. The diffusion rate may decrease or increase the delivery rate of the buprenorphine, a metabolite, or a prodrug thereof. When highly soluble organic liquids are used, they should diffuse from the delivery system over a period of seconds to hours. Under some circumstances, this rapid diffusion is responsible at least in part for the so-called burst effect. The burst effect is a short-lived but rapid release of buprenorphine, a metabolite, or a prodrug thereof upon implantation of the delivery system followed by a long-lived, slow release of buprenorphine, a metabolite, or a prodrug thereof.

Organic liquids used in the delivery system include, for example, aliphatic, aryl, and arylalkyl; linear, cyclic, and branched organic compounds that are liquid or at least flowable at ambient and physiological temperature and contain such functional groups as alcohols, alkoxylated alcohols, ketones, ethers, polymeric ethers, amides, esters, carbonates, sulfoxides, sulfones, any other functional group that is compatible with living tissue, and any combination thereof. The organic liquid preferably is a polar aprotic, or polar protic organic solvent. Preferably, the organic liquid has a molecular weight in the range of about 30 to about 1000.

Preferred biocompatible organic liquids that are at least slightly soluble in aqueous or body fluid include, for example, N-methyl-2-pyrrolidone, 2-pyrrolidone; (C1-C15) alcohols, diols, triols, and tetraols such as ethanol, glycerin, propylene glycol, and butanol; (C3-C15) esters and alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, and glyceryl triacetate; (C1-C15) amides such as dimethylformamide, dimethylacetamide, and caprolactam; (C3-C20 ethers such as tetrahydrofuran or solketal; tweens, triacetin, decylmethylsulfoxide, dimethyl sulfoxide, oleic acid, I-dodecylazacycloheptan-2-one, N-methyl-2-pyrrolidone, esters of carbonic acid and alkyl alcohols such as propylene carbonate, ethylene carbonate, and dimethyl carbonate; alcohols such as solketal, glycerol formal, and glycofurol; dialkylamides such as dimethylformamide, dimethylacetamide, dimethylsulfoxide, and dimethylsulfone; lactones such as epsilon-caprolactone and butyrolactone; cyclic alkyl amides such as caprolactam; triacetin and diacetin; aromatic amides such as N,N-dimethyl-m-toluamide; and mixtures and combinations thereof. Preferred solvents include, for example, N-methyl-2-pyrrolidone, 2-pyrrolidone, dimethylsulfoxide, ethyl lactate, propylene carbonate, solketal, triacetin, glycerol formal, isopropylidene glycol, and glycofurol.

Other preferred organic liquids are benzyl alcohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of their solvating ability and their compatibility.

The type and amount of biocompatible organic liquid present in the flowable composition should typically depend on the desired properties of the controlled release implant as described in detail below. Preferably, the flowable composition includes about 10 wt. % to about 90 wt. % or more preferably about 30 wt. % to about 70 wt. % of an organic liquid.

The solubility of the biodegradable thermoplastic polymers in the various organic liquids should differ depending upon their crystallinity, their hydrophilicity, hydrogen-bonding, and molecular weight. Lower molecular-weight polymers should normally dissolve more readily in the organic liquids than high-molecular-weight polymers. As a result, the concentration of a thermoplastic polymer dissolved in the various organic liquids should differ depending upon type of polymer and its molecular weight. Moreover, the higher molecular-weight thermoplastic polymers should tend to give higher solution viscosities than the low-molecular-weight materials.

When the organic liquid forms part of the flowable composition, it functions to enable easy, non-surgical placement of the sustained release delivery system into living tissue. It also facilitates transformation of the flowable composition to an in situ formed implant. Although it is not meant as a limitation of the invention, it is believed that the transformation of the flowable composition is the result of the dissipation of the organic liquid from the flowable composition into the surrounding body fluid and tissue and the infusion of body fluid from the surrounding tissue into the flowable composition. It is believed that during this transformation, the thermoplastic polymer and organic liquid within the flowable composition partition into regions rich and poor in polymer.

The pliability of the implant can be substantially maintained throughout its life if additives such as the organic liquid are maintained in the implant. Such additives also can act as a plasticizer for the thermoplastic polymer and at least in part may remain in the implant. One such additive having these properties is an organic liquid of low water solubility to water insolubility. Such an organic liquid providing these pliability and plasticizing properties may be included in the delivery system as the sole organic liquid or may be included in addition to an organic liquid that is moderately to highly water soluble. Organic liquids of low water solubility or water insolubility, such as those forming aqueous solutions of no more than about 5% by weight in water, can function as a pliability, plasticizing component, and in addition can act as the solvating component for the flowable composition embodiment. Such organic liquids can act as plasticizers for the thermoplastic polymer. When the organic liquid has these properties, it is a member of a subgroup of organic liquids termed "plasticizer." The plasticizer influences the pliablity and moldability of the implant composition such that it is rendered more comfortable to the patient when implanted. Moreover, the plasticizer has an effect upon the rate of sustained release of buprenorphine, a metabolite, or a prodrug thereof such that the rate can be increased or decreased according to the character of the plasticizer incorporated into the implant composition. In general, the organic liquid acting as a plasticizer is believed to facilitate molecular movement within the solid or gel thermoplastic matrix. The plasticizing capability enables polymer molecules of the matrix to move relative to each other so that pliability and easy moldability are provided. The plasticizing capability also enables easy movement of buprenorphine, a metabolite, or a prodrug thereof so that in some situations, the rate of sustained release is either positively or negatively affected.

High Water Solubility Organic Liquids

A moderate to highly water soluble organic liquid can be generally used in the flowable composition, especially when pliability should not be an issue after formation of the implant. Use of the highly water soluble organic liquid should provide an implant having the physical characteristics of an implant made through direct insertion of the flowable composition.

Use of a moderate to highly water soluble organic liquid in flowable composition should facilitate intimate combination and mixture of the other components therein. It should promote solid or gel homogeneity and pliability of an ex vivo formed implant so that such an implant can be readily inserted into appropriate incisions or trocar placements in tissue.

Useful, highly water soluble organic liquids include, for example, substituted heterocyclic compounds such as N-methyl-2-pyrrolidone (NMP) and 2-pyrrolidone; (C2-C10)alkanoic acids such as acetic acid and lactic acid, esters of hydroxy acids such as methyl lactate, ethyl lactate, alkyl citrates, and the like; monoesters of polycarboxylic acids such as monomethyl succinate acid, monomethyl citric acid, and the like; ether alcohols such as glycofurol, glycerol formal, isopropylidene glycol, and 2,2-dimethyl-1,3-dioxolone-4-methanol; Solketal; dialkylamides such as dimethylformamide and dimethylacetamide; dimethylsulfoxide (DMSO) and dimethylsulfone; lactones such as epsilon, caprolactone, and butyrolactone; cyclic alkyl amides such as caprolactam; and mixtures and combinations thereof. Preferred organic liquids include, for example, N-methyl-2-pyrrolidone, 2-pyrrolidone, dimethylsulfoxide, ethyl lactate, glycofurol, glycerol formal, and isopropylidene glycol.

Low Water Solubility Organic Liquids/Solvents

As described above, an organic liquid of low or no water solubility (hereinafter low/no liquid) may also be used in the sustained release delivery system. Preferably, a low/no liquid is used when it is desirable to have an implant that remains pliable, is to be extrudable is to have an extended release and the like. For example, the release rate of the biologically active agent can be affected under some circumstances through the use of a low/no liquid. Typically such circumstances involve retention of the organic liquid within the implant product and its function as a plasticizer or rate modifier. Suitable low or nonsoluble organic liquids include, for example, esters of carbonic acid and aryl alcohols such as benzyl benzoate; (C4-C10)alkyl alcohols; (C1-C6)alkyl(C2-C6)alkanoates; esters of carbonic acid and alkyl alcohols such as propylene carbonate, ethylene carbonate, and dimethyl carbonate, alkyl esters of mono-, di-, and tricarboxylic acids, such as 2-ethyoxyethyl acetate, ethyl acetate, methyl acetate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, and glyceryl triacetate; alkyl ketones such as methyl ethyl ketone; as well as other carbonyl, ether, carboxylic ester, amide, and hydroxy containing liquid organic compounds having some solubility in water. Propylene carbonate, ethyl acetate, triethyl citrate, isopropyl myristate, and glyceryl triacetate are preferred because of biocompatitibility and pharmaceutical acceptance. Additionally, mixtures of the foregoing high, low, or no solubility organic liquids providing varying degrees of solubility for the matrix forming material can be used to alter the life time, rate of bioactive agent release, and other characteristics of the implant. Examples include a combination of N-methyl-2-pyrrolidone and propylene carbonate, which provides a more hydrophobic solvent than N-methyl-2-pyrrolidone alone, and a combination of N-methyl-2-pyrrolidone and polyethylene glycol, which provides a more hydrophilic solvent than N-methyl-2-pyrrolidone alone.

The organic liquid for inclusion in the composition should be biocompatible. Biocompatible means that as the organic liquid disperses or diffuses from the composition, it does not result in substantial tissue irritation or necrosis surrounding the implant site.

Organic Liquid for the Preferred Flowable Composition

For the preferred flowable composition incorporating a thermoplastic polyester, any suitable polar aprotic organic liquid can be employed, provided that the suitable polar aprotic solvent displays a body fluid solubility within a range of completely soluble in all proportions to very slightly soluble. Suitable polar aprotic organic liquids are disclosed, e.g., in ALDRICH HANDBOOK OF FINE CHEMICALS AND LABORATORY EQUIPMENT, Milwaukee, Wis. (2000) and in U.S. Pat. Nos. 5,324,519, 4,938,763, 5,702,716, 5,744,153, and 5,990,194. A suitable polar aprotic liquid should be able to diffuse over time into body fluid so that the flowable composition coagulates or solidifies. The diffusion may be rapid or slow. It is also preferred that the polar aprotic liquid for the biodegradable polymer be non-toxic and otherwise biocompatible.

The polar aprotic organic liquid is preferably biocompatible. Suitable polar aprotic organic liquid include, for example, those having an amide group, an ester group, a carbonate group, a ketone, an ether, a sulfonyl group, or a combination thereof. Preferably, the polar aprotic organic liquid comprises N-methyl-2-pyrrolidone, 2-pyrrolidone, N,N-dimethylformamide, dimethyl sulfoxide, propylene carbonate, caprolactam, triacetin, or any combination thereof. More preferably, the polar aprotic organic solvent is N-methyl-2-pyrrolidone.

The solubility of the biodegradable thermoplastic polyesters in the various polar aprotic liquids should differ depending upon their crystallinity, their hydrophilicity, hydrogen-bonding, and molecular weight. Thus, not all of the biodegradable thermoplastic polyesters should be soluble to the same extent in the same polar aprotic organic liquid, but each biodegradable thermoplastic polymer or copolymer should be soluble in its appropriate polar aprotic solvent. Lower molecular-weight polymers should normally dissolve more readily in the liquids than high-molecular-weight polymers. As a result, the concentration of a polymer dissolved in the various liquids should differ depending upon type of polymer and its molecular weight. Conversely, the higher molecular-weight polymers should normally tend to coagulate or solidify faster than the very low-molecular-weight polymers. Moreover the higher molecular-weight polymers should tend to give higher solution viscosities than the low-molecular-weight materials.

For example, low-molecular-weight polylactic acid formed by the condensation of lactic acid should dissolve in N-methyl-2-pyrrolidone (NMP) to give about 73% by weight solution which still flows easily through a 23-gauge syringe needle, whereas a higher molecular-weight poly(DL-lactide) (DL-PLA) formed by the additional polymerization of DL-lactide gives the same solution viscosity when dissolved in N-methyl-2-pyrrolidone at about 50% by weight. The higher molecular-weight polymer solution coagulates immediately when placed into water. The low-molecular-weight polymer solution, although more concentrated, tends to coagulate very slowly when placed into water.

It has also been found that solutions containing very high concentrations of high molecular weight polymers sometimes coagulate or solidify slower than more dilute solutions. It is believed that the high concentration of polymer impedes the diffusion of solvent from within the polymer matrix and consequently prevents the permeation of water into the matrix where it can precipitate the polymer chains. Thus, there is an optimum concentration at which the solvent can diffuse out of the polymer solution and water penetrates within to coagulate the polymer.

The concentration and species of the polar aprotic organic liquid for the preferred flowable composition incorporating a thermoplastic polyester should typically depend upon the desired properties of the controlled release implant. For example, the species and amount of biocompatible polar aprotic solvent can influence the length of time in which the buprenorphine, a metabolite, or a prodrug thereof is released from the controlled release implant.

Specifically, in one embodiment, the flowable composition can be used to formulate a one month delivery system of buprenorphine, a metabolite, or a prodrug thereof. In such an embodiment, the biocompatible polar aprotic solvent can preferably be N-methyl-2-pyrrolidone and can preferably present in about 30 wt. % to about 70 wt. % of the composition.

Alternatively, in another embodiment, the composition can be used to formulate a three month delivery system of buprenorphine, a metabolite, or a prodrug thereof. In such an embodiment, the biocompatible polar aprotic solvent can preferably be N-methyl-2-pyrrolidone and can preferably present in about 30 wt. % to about 70 wt. % of the composition.

Buprenorphine

Buprenorphine (also known as (2S)-2-[(−)-(5R,6R,7R,14S)-9α-cyclo-propyl-methyl-4,5-epoxy-6,14-ethano-3-hydroxy-6-methoxymorphinan-7-yl]-3,3-di-methylbutan-2-ol and marketed under the trade names SUBUTEX™ and SUBOXONE™ is an opioid agonist agent belonging to the chemical class of thebaine derivatives. Buprenorphine, a metabolite, or a prodrug thereof may be administered in its unneutralized basic form, or as a salt of an organic or inorganic acid. Examples include the buprenorphine, a metabolite, or a prodrug thereof salts wherein the gegenion (counterion) is acetate, propionate, tartrate, malonate, chloride, sulfate, bromide, and other pharmaceutically acceptable organic and inorganic acid gegenions.

Buprenorphine, a metabolite, or a prodrug thereof may be lyophilized prior to use. Typically, the buprenorphine, a metabolite, or a prodrug thereof may be dissolved in an aqueous solution, sterile filtered, and lyophilized in a syringe. In a separate process, the thermoplastic polymer/organic liquid solution can be filled into second syringe. The two syringes can be coupled together and the contents can be drawn back and forth between the two syringes until the thermoplastic polymer, organic liquid, and the buprenorphine, a metabolite, or a prodrug thereof are effectively mixed together, forming a flowable composition. The flowable composition can be drawn into one syringe. The two syringes can be disconnected and a needle attached to the syringe containing the flowable composition. The flowable composition can be injected through the needle into the body. The flowable composition can be formulated and administered to a patient as described in, e.g., U.S. Pat. Nos. 5,324,519, 4,938,763, 5,702,716, 5,744,153, and 5,990,194; or as described herein. Once administered, the organic liquid dissipates, the remaining polymer gels or solidifies, and a matrix structure is formed. The organic liquid should dissipate and the polymer should solidify or gel so as to entrap or encase the buprenorphine, a metabolite, or a prodrug thereof within the matrix.

The release of buprenorphine, a metabolite, or a prodrug thereof from the implant should follow the same general rules for release of a drug from a monolithic polymeric device. The release of buprenorphine, a metabolite, or a prodrug thereof can be affected by the size and shape of the implant, the loading of buprenorphine, a metabolite, or a prodrug thereof within the implant, the permeability factors involving the buprenorphine, a metabolite, or a prodrug thereof and the particular polymer, and the degradation of the polymer. Depending upon the amount of buprenorphine, a metabolite, or a prodrug thereof selected for delivery, the above parameters can be adjusted by one skilled in the art of drug delivery to give the desired rate and duration of release.

The amount of buprenorphine, a metabolite, or a prodrug thereof incorporated into the sustained release delivery system depends upon the desired release profile, the concentration of buprenorphine, a metabolite, or a prodrug thereof used for a biological effect, and the length of time that the buprenorphine, a metabolite, or a prodrug thereof has to be released for treatment. There is no upper limit on the amount of buprenorphine, a metabolite, or a prodrug thereof incorporated into the sustained release delivery system except for that of an acceptable solution or dispersion viscosity for injection through a syringe needle. The lower limit of buprenorphine, a metabolite, or a prodrug thereof incorporated into the sustained release delivery system is dependent upon the activity of the buprenorphine, a metabolite, or a prodrug thereof and the length of time needed for treatment. Specifically, in one embodiment, the sustained release delivery system can be formulated to provide a one month release of buprenorphine, a metabolite, or a prodrug thereof. In such an embodiment, the buprenorphine, a metabolite, or a prodrug thereof can preferably be present in about 0.5 wt. % to about 50 wt. %, preferably about 1 wt. % to about 30 wt. % of the composition. Alternatively, in another embodiment, the sustained release delivery system can be formulated to provide a three month delivery of buprenorphine, a metabolite, or a prodrug thereof. In such an embodiment, the buprenorphine, a metabolite, or a prodrug thereof can preferably be present in about 0.5 wt. % to about 50 wt. %, preferably about 1 wt. % to about 30 wt. % of the composition. The gel or solid implant formed from the flowable composition should release the buprenorphine, a metabolite, or a prodrug thereof contained within its matrix at a controlled rate until the implant is effectively depleted of buprenorphine, a metabolite, or a prodrug thereof.

Adjuvants and Carriers

The sustained release delivery system may include, for example, a release rate modifier to alter the sustained release rate of buprenorphine, a metabolite, or a prodrug thereof from the implant matrix. The use of a release rate modifier may either decrease or increase the release of buprenorphine, a metabolite, or a prodrug thereof in the range of several times of differences as compared to the release of buprenorphine, a metabolite, or a prodrug thereof from an implant matrix without the release rate modifier.

With the addition of a hydrophobic release rate modifier such as hydrophobic ethyl heptanoate, to the sustained release delivery system, and formation of the implant matrix through interaction of the flowable composition and body fluid, the release rate of buprenorphine, a metabolite, or a prodrug thereof can be slowed. Hydrophilic release rate modifiers such as polyethylene glycol may increase the release of the buprenorphine, a metabolite, or a prodrug thereof. By an appropriate choice of the polymer molecular weight in combination with an effective amount of the release rate modifier, the release rate and extent of release of a buprenorphine, a metabolite, or a prodrug thereof from the implant matrix may be varied, for example, from relatively fast to relatively slow.

Useful release rate modifiers include, for example, organic substances which are water-soluble, water-miscible, or water insoluble (i.e., hydrophilic to hydrophobic).

The release rate modifier is preferably an organic compound which is thought to increase the flexibility and ability of the polymer molecules and other molecules to slide past each other even though the molecules are in the solid or highly viscous state. It is preferred that a release rate modifier is compatible with the combination of polymer and organic liquid used to formulate the sustained release delivery system. It is further preferred that the release rate modifier is a pharmaceutically-acceptable substance.

Useful release rate modifiers include, for example, fatty acids, triglycerides, other like hydrophobic compounds, organic liquids, plasticizing compounds, and hydrophilic compounds. Suitable release rate modifiers include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl)sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as (C6-C12)alkanols, 2-ethoxyethanol, and the like. The release rate modifier may be used singly or in combination with other such agents. Suitable combinations of release rate modifiers include, for example, glycerin/propylene glycol, sorbitol/glycerin, ethylene oxide/propylene oxide, butylene glycol/adipic acid, and the like. Preferred release rate modifiers include, for example, dimethyl citrate, triethyl citrate, ethyl heptanoate, glycerin, and hexanediol.

The amount of the release rate modifier included in the flowable composition should vary according to the desired rate of release of the buprenorphine, a metabolite, or a prodrug thereof from the implant matrix. Preferably, the sustained release delivery system contains about 0.5 to about 30%, preferably about 5 to about 10%, of a release rate modifier.

Other solid adjuvants may also be optionally combined with the sustained release delivery system to act as carriers, especially isolation carriers. These include, for example, additives or excipients such as a starch, sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, and/or polyvinylpyrrolidone.

Additional adjuvants may include, for example, oils such as peanut oil, sesame oil, cottonseed oil, corn oil, and olive oil as well as esters of fatty acids such as ethyl oleate, isopropyl myristate, fatty acid glycerides, and acetylated fatty acid glycerides. Also included are alcohols, such as, but not limited to, ethanol, isopropyl alcohol, hexadecyl alcohol, glycerol, and propylene glycol. Ethers, such as but not limited to, poly(ethyleneglycol); petroleum hydrocarbons such as mineral oil and petrolatum may also be used in the formulations. Pectins, carbomers, methyl cellulose, hydroxypropyl cellulose, hydroxypropyl methyl cellulose, or carboxymethyl cellulose may also be included. These compounds can serve as isolation carriers by coating the buprenorphine, a metabolite, or a prodrug thereof thereby preventing its contact with the organic solvent and other ingredients of the flowable composition. As isolation carriers, these compounds also help lower the burst effect associated with the coagulation of the flowable composition in situ.

Optionally, other compounds such as, but not limited to, stabilizers, antimicrobial agents, antioxidants, pH modifiers, bioavailability modifiers, and combinations of these are included. Emulsifiers and surfactants such as fatty acids or a non-ionic surfactants including natural or synthetic polar oil, fatty acid esters, polyol ethers, and mono-, di-, or tri-glycerides may also be included.

The Implant

When the implant is formed, the implant has the physical state of a solid. The solid embodiments may be rigid so that they cannot be flexed or bent by squeezing them between the fingers or they may be flexible or bendable so that they can be compressed or flexed out of original shape by squeezing between the fingers (i.e., a low amount of force). The thermoplastic polymer functions as a matrix in these embodiments to provide integrity to the single body solid and to enable controlled release of the bioactive agent upon implantation.

The thermoplastic polymer matrix is preferably a solid matrix and especially preferably is microporous. In an embodiment of the microporous solid matrix, there is a core surrounded by a skin. The core preferably contains pores of diameters from about 1 to about 1000 microns. The skin preferably contains pores of smaller diameters than those of the core pores. In addition, the skin pores are preferably of a size such that the skin is functionally non-porous in comparison with the core.

Because all of the components of the implant are biodegradable or can be swept away from the implant site by body fluid and eliminated from the body, the implant eventually disappears. The implant components may complete their biodegradation or disappearance before, after or at the same time as the buprenorphine, a metabolite, or a prodrug thereof has been typically completely released. The structure of the thermoplastic polymer, its molecular weight, the density and porosity of the implant, and the body location of the implant all affect the biodegradation and disappearance rates. The implant is typically formed subcutaneously in a patient. It can be molded in place upon injection to provide comfort to the patient. The implant volume typically may be between about 0.25 mL to about 3 mL in size.

Therapeutic Use

Surprisingly, it has been discovered that the sustained release delivery system is highly effective in delivering buprenorphine. Specifically, as shown in the Examples below, the blood levels of buprenorphine obtained with the sustained release delivery system are from about 0.5 nanograms per milliliter (ng/mL) to about 20 ng/mL in dogs after a 60 mg buprenorphine dose injection in beagles.

In general, any disease which may be ameliorated, treated, cured, or prevented by administration of buprenorphine, a metabolite, or a prodrug thereof or a buprenorphine analog may be treated by administration of the flowable composition. These diseases relate to mental impairments. The following specific malconditions are exemplary of such diseases. These may all be treated by appropriate, effective administration of a flowable composition formulated to deliver an effective amount of buprenorphine, a metabolite, or a prodrug thereof. These malconditions include: addiction to opioid substances and chronic pain, and the like.

Dosages

The amount of flowable composition administered should typically depend upon the desired properties of the controlled release implant. For example, the amount of flowable composition can influence the length of time in which the buprenorphine, a metabolite, or a prodrug thereof is released from the controlled release implant. Specifically, in one embodiment, the composition can be used to formulate a one month delivery system of buprenorphine, a metabolite, or a prodrug thereof, hi such an embodiment, about 0.20 mL to about 2.0 mL of the flowable composition can be administered. Alternatively, in another embodiment, the composition can be used to formulate a three month delivery system of buprenorphine, a metabolite, or a prodrug thereof. In such an embodiment, about 0.5 mL to about 2.0 mL of the flowable composition can be administered. The amount of buprenorphine, a metabolite, or a prodrug thereof within the flowable composition and the resulting implant should depend upon the disease to be treated, the length of duration desired, and the bioavailability profile of the implant. Generally, the effective amount should be within the discretion and wisdom of the patient's attending physician. Guidelines for administration include, for example, dose ranges of from about 1 to about 16 milligrams (mg) of buprenorphine, a metabolite, or a prodrug thereof per day, preferably from about 1 to about 5 milligrams (mg) of buprenorphine, a metabolite, or a prodrug thereof per day, as applied for The typical flowable composition effective for such sustained delivery over a 1 month period should contain from about 3 to about 300 mg of buprenorphine, a metabolite, or a prodrug thereof per ml of total volume of flowable composition. The injection volume should range from about 0.2 to about 2.0 mL per implant. The typical flowable composition effective for such sustained delivery of a 3 month period should contain from about 9 to about 900 mg of buprenorphine, a metabolite, or a prodrug thereof per ml of total volume of flowable composition. The injection volume should range from 0.5 to about 2.0 mL per implant. The polymer formulation should be the primary factor for obtaining the longer sustained release, as discussed above.

All publications, patents, and patent documents are incorporated by reference herein, as though individually incorporated by reference. The invention should now be illustrated with the following non-limiting examples. The following Examples employ the ATRIGEL™ formulation of poly(lactide-co-glycolide) and N-methyl-2-pyrrolidone in combination with buprenorphine as the flowable composition.

EXAMPLES

In the following Examples, ATRIGEL™/Buprenorphine refers to ATRIGEL™/Buprenorphine formulations; ATRIGEL™ is a registered Trademark of QLT-USA, Fort Collins, Colo. The particular form of ATRIGEL™ product used in these examples is provided with the examples. Unless otherwise indicated, the ATRIGEL™ product is the thermoplastic polymer poly(lactide-co-glycolide) (PLG), the thermoplastic polymer poly(lactide-co-glycolide extended with 1,6-hexane diol) (PLG), or PLGH in the organic solvent N-methyl-2-pyrrolidone. SUBUTEX™ and SUBUTEX™ are registered Trademarks of Janssen, L. P., Titusville, N.J.

The ATRIGEL™ drug delivery system is a biodegradable polymeric delivery system that can be injected as a liquid. Upon injection of the formulation, the polymer solidifies encapsulating the drug. As the process of biodegradation begins, the drug is slowly released. The release rate of drugs from this type of delivery system can be controlled by the type and molecular weight of the polymer and drug load of the constituted product. Therefore, the system can be tailored to meet the needs of the patient.

The ATRIGEL™ Delivery System is currently used in the Food and Drug Administration approved products ELIGARD™ (one, three, and four-month subcutaneous depot formulations of leuprolide acetate) and ATRIDOX™ (doxycycline hyclate applied to the periodontal pocket). Clinical studies and post-marketing experience with these products demonstrate that the ATRIGEL™ Delivery System itself is well tolerated and provides consistent, sustained release of the incorporated drug over the designated dosing period.

These features represent improvements regardless of the particular application, i.e. any buprenorphine responsive disease.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Test Procedures

Preparation of Polymer Solutions

Polymer stock solutions were prepared by weighing a known amount of each polymer solid into individual 20 mL scintillation vials. A known amount of N-methyl-2-pyrrolidone was added to each polymer and the vials were placed on a horizontal jar mill. The vials were rotated overnight (possibly over several days) to produce a visually clear polymer solution indicating dissolution of the polymer. Sterilization of the polymer solution may have been accomplished by gamma irradiation or electron beam irradiation.

Preparation of Test Article Syringes

The "B" syringes (male syringes) contained buprenorphine powder and were prepared by weighing drug powder into 3.00 mL Becton Dickinson (BD) male syringes. The "A" syringes (female syringes) were prepared by weighing ATRIGEL™ polymer stock solutions into 1.0 mL female syringes.

Preparation of Test Articles (Reconstituted Formulation) for Injection

Immediately prior to injection, "A" and "B" syringes were coupled and mixed by cycling the contents from one syringe to the other for 60 cycles. The mixed formulation was finally transferred to the male dosing syringe for injection. Formulations may also be prepared by dissolving buprenorphine in ATRIGEL™ polymer stock solutions. In this case, buprenorphine and selected ATRIGEL™ were weighed into a scintillation vial, and the vial was shaken and/or heated briefly to completely dissolve buprenorphine. The resulting drug ATRIGEL™ solution was then filled into dosing syringes for injections.

Reversed Phase High Performance Liquid Chromatography Method for the Quantization of Buprenorphine The High Performance Liquid Chromatography had the following conditions: Mobile Phase A: 0.065% sodium octanesulfonic acid and 0.1% trifluoroacetic acid in water; Mobile Phase B: 90/10 acetonitrile/0.065% sodium octanesulfonic acid and 0.1% trifluoroacetic acid in water; flow rate: 1.0 ml/min; autosampler temperature: room temperature; column temperature: 30° C.; detection: 285 run (UV); total run time: 21 min; injection volume: 20 µL; column: Phenomenex Luna C18 250×4.6 mm, 5 µm; column storage: 70/30 acetonitrile/water; each sample run according to the following gradient program:

| Time | Mobile Phase A | Mobile Phase B |
|------|----------------|----------------|
| 0    | 100%           | 0%             |
| 2    | 100%           | 0%             |
| 16   | 20%            | 80%            |
| 18   | 0%             | 100%           |
| 20   | 100%           | 0%             |
| 21   | 100%           | 0%             | approximate retention time of buprenorphine: 15.4 minutes.

The standard solution preparation is as follows: standard stock solution was made by dissolving approximately 10 mg buprenorphine in 10 mL 1:1 formulation dissolution solution [90/5/5 acetonitrile/glacial acetic acid/water]/H2O. A series standards ranging from 40 ppm to 500 ppm was diluted with water from the standard stock solution.

Implant Extraction Procedure for Implant Retrieval Study

The freshly retrieved implants were carefully debrided the tissues surrounding the implants using a surgical blade or scissor. The implants could be analyzed immediately thereafter or stored in a −20° C. freezer until a later time. At the time of analysis, exactly 10 mL of the formulation dissolution solution [90/5/5 acetonitrile/glacial acetic acid/water] was added to the implant vial. The vials were then shaken at about 200 rpm at room temperature on the orbital shaker for at least 2 hours. The vials were then centrifuged at 2500 rpm for 10 minutes. After centrifuge, the vials were carefully removed from the centrifuge. A portion of the supernatant from the vial was transferred into a HPLC vial and if necessary, the transferred solution in the vial was further diluted using the formulation dissolution solution to a suitable concentration for HPLC analysis. The vials were then analyzed for buprenorphine content by the High Performance Liquid Chromatography method as described above.

Buprenorphine Analysis in Rat Plasma Samples

This procedure was adopted from Li-Heng Pao et al., Journal of Chromatography B, 746 (2000), 241-247. To 1 mL or proper amount of the rat plasma sample, 20 µl of internal standard [buprenorphine acid rearrangement product, RX2001M, supplied by RBP], 1 mL 0.5 M sodium bicarbonate solution, and 3 mL of mixture of n-hexane-isoamyl alcohol (9:1 v/v) were added. The solution was then agitated in a shaker at 200 rpm at room temperature for at least 30 minutes. After centrifugation for 10 minutes at 3000 rpm, the solution was placed in a −86° C. freezer for 30 minutes. The top organic layer was then transferred to a clean tube and evaporated to dryness under a steam of nitrogen at 65° C. The sample was reconstituted in 200 µL mobile phase and an aliquot of 50 µL was injected onto the column.

The High Performance Liquid Chromatography had the following conditions: Mobile Phase: 80/20 acetonitrile/5 mM sodium acetate buffer (pH 3.75); flow rate: 1.2 mL/min; autosampler temperature: room temperature; column temperature: 25° C.; detection: fluorescence (excitation at 215 nm and emission at 355 nm); total run time: 14 min; injection volume: 50 µL; column: Phenomenex Luna Silica (2) 250× 4.6 mm, 5 µm; column storage: 100% acetonitrile; approximate retention time for buprenorphine and the internal standard: 7.9 min and 8.7 min.

Buprenorphine and Norbuprenorphine Analysis in Dog Plasma Samples

Plasma samples from dog studies were analyzed for buprenorphine and norbuprenorphine levels using a LC-MS-MS method through a contract analytical service laboratory. The method was developed and validated by the contracted laboratory. It was a proprietary method that employed a liquid-liquid extraction step followed by LC-MS-MS analysis.

In Vivo Animal Studies

Experimental Procedures: All rat preclinical studies were conducted in male Sprague-Dawley rats. Five rats per Test Article per time point were injected either intramuscularly or subcutaneously under full anesthesia in the dorsal thoracic (DT) region with approximately 100 mg of the Test Article, described above.

During the course of the study, the animals were observed for overt toxicity and any existing test site abnormalities, including redness, bleeding, swelling, discharge, bruising and Test Article extrusion at the injection site were observed and recorded. In addition, injection weights were recorded at administration and body weights were taken and recorded at administration and at termination. If blood samples were taken for the study, at selected time points, five rats per Test Article were anesthetized and bled (about 5 mL) via cardiac puncture. Blood was collected in labelled potassium ethylenediaminetetraacetic acid tubes. The blood was centrifuged for 10 min at 3000 rpm. The plasma fraction was transferred to labelled 5 mL plastic culture tubes and stored at −86° C. The plasma was analyzed using the liquid-liquid extraction method described above.

After blood collection or if no blood samples were required for the study, the animals were terminated with carbon dioxide and the implants were retrieved. The implants were debrided excess tissue and were stored at −20° C. until analysis. The retrieved implants were analyzed for buprenorphine content using the implant analysis method described above.

Pharmacokinetics studies in large animals were performed in male beagle dogs. Male beagles with body weights between 8 to 12 kg were selected in these studies. Six dogs per group were injected subcutaneously in the dorsal thoracic region at a buprenorphine equivalent dose of 60 mg per dog. Exact injection doses were obtained by weighing the injection syringe before and after each injection. After injection, the dogs were bled periodically to collect their plasma samples. All plasma samples were stored in a −80° C. freezer until analysis. The animals were also watched periodically for any sign of toxicity as well as injection site reactions.

Buprenorphine and norbuprenorphine levels in dog plasma samples were measured using a validated LC/MS/MS method through a qualified contract analytical laboratory as described above.

Example 1

24-Hour Burst Release of Buprenorphine ATRIGEL™ in Rats

Eight buprenorphine ATRIGEL™ formulations were prepared according to the methods described above. The buprenorphine hydrochloride formulations had the two-syringe configuration and the buprenorphine free base formulations were solutions. The eight formulations had the following compositions.

Test Articles for Example 1:
1. 10% buprenorphine hydrochloride in 45% 50/50 PLGH (26 kD) and 55% NMP
2. 10% buprenorphine hydrochloride in 55% 65/35 PLGH (17 kD) and 45% NMP
3. 10% buprenorphine hydrochloride in 48% 55/45 PLG (22 kD), 2% PEG5000-70/30 PLG (59 kD) and 50% NMP
4. 10% buprenorphine free base in 45% 50/50 PLGH (26 kD) and 55% NMP
5. 10% buprenorphine free base in 50% 65/35 PLGH (17 kD) and 50% NMP
6. 10% buprenorphine free base in 55% 65/35 PLGH (17 kD) and 45% NMP
7. 10% buprenorphine free base in 50% 55/45 PLG (22 kD) and 50% NMP
8. 10% buprenorphine free base in 48% 55/45 PLG (22 kD), 2% PEG5000-70/30 PLG (59 kD) and 50% NMP Their initial release in 24 hours (initial burst) is shown in Table 1. All formulations had low initial burst less than 10%.

TABLE 1

Buprenorphine 24-hour release (initial burst) after subcutaneous injection of ATRIGEL ™ formulations in rats

| TA | 24-Hour Release % | Standard deviation |
|---|---|---|
| 1 | 4.6 | 3.7 |
| 2 | 3.1 | 2.2 |
| 3 | 2.2 | 4.0 |
| 4 | 7.5 | 1.6 |
| 5 | 7.2 | 0.7 |
| 6 | 5.5 | 1.0 |
| 7 | 4.4 | 4.6 |
| 8 | 8.8 | 0.7 |

Example 2

49-Day Buprenorphine Release from Buprenorphine Hydrochloride ATRIGEL™ in Rats

Three buprenorphine hydrochloride ATRIGEL™ formulations were prepared using the NB two-syringe configuration. They were injected subcutaneously in a total of 135 male SD rats. At each time points, five rats per group were euthanized and the implants were retrieved. The time points were 2 hour, 1, 7, 14, 21, 28, 35, 42 and 49 days. The formulations and the buprenorphine release profiles were shown in Table 2 and FIG. 2.

Test Articles for Example 2
1. 20% buprenorphine hydrochloride in 50% 50/50 PLGH (15 kD) and 50% NMP
2. 20% buprenorphine hydrochloride in 50% 65/35 PLGH (10 kD) and 50% NMP
3. 20% buprenorphine hydrochloride in 50% 65/35 PLGH (17 kD) and 50% NMP

TABLE 2

Buprenorphine release after suncutaneous injection of buprenorphine hydrochloride ATRIGEL ™ formulations in rats

| Time (Day) | TA 1 | Standard Deviation | TA 2 | Standard Deviation | TA 3 | Standard Deviation |
|---|---|---|---|---|---|---|
| 0.0833 | 1.9 | 1.1 | 5.5 | 3.0 | −0.6 | 1.9 |
| 1 | 1.2 | 3.2 | 5.8 | 0.9 | −0.2 | 1.7 |
| 7 | 11.5 | 4.4 | 12.3 | 1.4 | 13.2 | 4.2 |
| 14 | 10.6 | 7.2 | 17.8 | 3.5 | 15.5 | 14.3 |
| 21 | 36.1 | 11.6 | 37.3 | 14.2 | 14.7 | 2.0 |
| 28 | 56.0 | 13.9 | 66.2 | 8.3 | 32.3 | 6.2 |
| 35 | 72.0 | 11.9 | 73.8 | 13.1 | 42.8 | 4.2 |
| 42 | 81.4 | 9.0 | 85.8 | 2.9 | 64.1 | 11.4 |
| 49 | 82.6 | 15.2 | 87.6 | 9.0 | 63.9 | 16.5 |

Example 3

35-Day Buprenorphine Release and Pharmacokinetic Profiles from Buprenorphine Free Base ATRIGEL™ in Rats Four buprenorphine free base ATRIGEL™ formulations were prepared as solutions in ready-to-inject syringes. They were injected subcutaneously in a total of 160 male SD rats. At each time points, five rats per group were anesthetized and blood samples were taken by cardiac puncture. The rats were then euthanized and the implants were retrieved. Both the retrieved implants and plasma samples were analyzed for buprenorphine as described above. The results are shown in FIG. 3 and FIG. 4.

Test Articles for Examples 3
1. 15% buprenorphine free base in 45% 50/50 PLGH (26 kD) and 55% NMP
2. 20% buprenorphine free base in 40% 50/50 PLGH (17 kD) and 50% NMP
3. 20% buprenorphine free base in 20% 50/50 PLGH (26 kD), 20% 50/50 PLGH (12 kD), and 60% NMP
4. 20% buprenorphine free base in 45% 50/50 PLGH (12 kD) and 55% NMP

TABLE 3

Buprenorphine release after suncutaneous injection of buprenorphine free base ATRIGEL ™ formulations in rats

| Time (Day) | TA 1 | Standard Deviation | TA 2 | Standard Deviation | TA 3 | Standard Deviation | TA 4 | Standard Deviation |
|---|---|---|---|---|---|---|---|---|
| 0.0833 | 2.6 | 0.8 | 1.9 | 0.7 | 2.2 | 0.3 | 2.6 | 0.7 |
| 3 | 8.8 | 1.7 | 7.2 | 1.4 | 7.3 | 1.3 | 6.5 | 1.2 |
| 7 | 16.5 | 1.6 | 13.7 | 2.0 | 13.6 | 2.0 | 13.0 | 2.6 |

TABLE 3-continued

Buprenorphine release after suncutaneous injection of buprenorphine free base ATRIGEL ™ formulations in rats

| Time (Day) | TA 1 | Standard Deviation | TA 2 | Standard Deviation | TA 3 | Standard Deviation | TA 4 | Standard Deviation |
|---|---|---|---|---|---|---|---|---|
| 14 | 35.8 | 5.0 | 28.9 | 6.9 | 32.2 | 7.9 | 25.1 | 6.7 |
| 17 | 50.0 | 14.2 | 38.2 | 7.1 | 29.7 | 5.4 | 43.2 | 5.3 |
| 21 | 49.1 | 13.0 | 45.1 | 12.1 | 41.6 | 9.4 | 44.3 | 10.2 |
| 28 | 61.2 | 8.3 | 58.2 | 7.7 | 62.9 | 13.7 | 59.0 | 15.5 |
| 35 | 78.7 | 13.7 | 64.0 | 8.6 | 63.6 | 15.3 | 74.7 | 8.6 |

TABLE 4

Plasma buprenorphine levels after subcutaneous injection of buprenorphine free base ATRIGEL ™ formulations in rats

| Time (Day) | TA 1 | Standard Deviation | TA 2 | Standard Deviation | TA 3 | Standard Deviation | TA 4 | Standard Deviation |
|---|---|---|---|---|---|---|---|---|
| 0.0833 | 44.9 | 17.5 | 54.4 | 21.3 | 64.5 | 19.6 | 93.3 | 27.8 |
| 3 | 11.4 | 1.9 | 10.8 | 1.7 | 14.5 | 3.6 | 16.9 | 2.0 |
| 7 | 16.4 | 2.4 | 22.4 | 5.1 | 21.5 | 4.7 | 22.0 | 7.7 |
| 14 | 27.9 | 7.9 | 22.7 | 5.1 | 34.9 | 11.1 | 31.0 | 15.0 |
| 17 | 31.0 | 4.9 | 39.7 | 10.6 | 30.1 | 11.0 | 44.5 | 13.8 |
| 21 | 20.0 | 2.9 | 28.6 | 9.0 | 22.9 | 3.6 | 24.3 | 9.2 |
| 28 | 18.3 | 5.1 | 26.6 | 4.9 | 20.3 | 3.8 | 20.0 | 2.9 |
| 35 | 13.6 | 1.7 | 17.5 | 4.7 | 14.6 | 6.1 | 13.7 | 1.8 |

Example 4

Pharmacokinetic Study of Two Buprenorphine Hydrochloride ATRIGEL™ in Dogs

Two buprenorphine hydrochloride ATRIGEL™ formulations were prepared using the A/B two-syringe configuration. They were injected subcutaneously in a total of 12 male beagle dogs. The dogs were then bled regularly at each time point to collect their plasma samples. The plasma samples were analyzed using a validated LC/MS/MS method by a contract analytical service company.

Test Articles for Example 4
TA 1: 20% buprenorphine hydrochloride in 50% 50/50 PLGH (12 kD) and 50% NMP
TA 2: 20% buprenorphine hydrochloride in 50% 50/50 PLGH (21 kD) and 50% NMP

TABLE 5

Mean plasma buprenorphine levels after subcutaneous injection of two buprenorphine hydrochloride ATRIGEL ™ formulations in Beagles

| Time Points (Day) | TA #1 (ng/mL) |
|---|---|
| Day 0 Hr 1 | 12.10 ± 5.42 |
| Day 0 Hr 2 | 12.83 ± 3.82 |
| Day 0 Hr 4 | 7.64 ± 1.57 |
| Day 0 Hr 8 | 4.31 ± 1.20 |
| 1 | 3.63 ± 1.13 |
| 2 | 3.42 ± 1.54 |
| 3 | 2.31 ± 0.57 |
| 4 | 1.88 ± 0.51 |
| 7 | 2.77 ± 1.06 |
| 10 | 4.15 ± 1.45 |
| 14 | 7.51 ± 5.31 |
| 17 | 7.54 ± 4.88 |
| 21 | 3.93 ± 3.17 |
| 24 | 1.73 ± 1.10 |
| 28 | 0.90 ± 0.50 |
| 31 | 0.67 ± 0.51 |
| 35 | 0.58 ± 0.52 |
| 38 | 0.46 ± 0.50 |
| 42 | 0.26 ± 0.30 |
| 45 | 0.35 ± 0.42 |
| 56 | 0.26 ± 0.31 |
| 63 | 0.23 ± 0.29 |
| 70 | 0.27 ± 0.36 |
| 77 | 0.29 ± 0.44 |
| 84 | 0.33 ± 0.52 |
| 91 | 0.28 ± 0.43 |
| 102 | 0.18 ± 0.29 |
| 120 | 0.22 ± 0.37 |
| 147 | 0.17 ± 0.31 |
| 183 | 0.12 ± 0.17 |

| Time Points (Day) | TA #2 (ng/mL) |
|---|---|
| Day 0 Hr 1 | 11.80 ± 6.40 |
| Day 0 Hr 2 | 12.08 ± 3.80 |
| Day 0 Hr 4 | 7.26 ± 1.51 |
| Day 0 Hr 8 | 3.85 ± 0.83 |
| 1 | 2.94 ± 0.76 |
| 3 | 1.29 ± 0.28 |
| 7 | 1.36 ± 0.52 |
| 10 | 1.75 ± 0.62 |
| 14 | 2.30 ± 1.24 |
| 17 | 3.97 ± 2.33 |
| 20 | 2.90 ± 1.48 |
| 24 | 2.45 ± 0.73 |
| 27 | 1.98 ± 0.94 |
| 31 | 1.71 ± 0.94 |
| 38 | 1.28 ± 0.52 |
| 45 | 0.94 ± 0.24 |
| 52 | 0.71 ± 0.11 |
| 66 | 0.47 ± 0.19 |
| 80 | 0.38 ± 0.22 |
| 122 | 0.20 ± 0.07 |

Example 5

Pharmacokinetic Study of Four Buprenorphine Free Base ATRIGEL™ in Dogs

Four buprenorphine free base ATRIGEL™ formulations were prepared as solutions in ready-to-inject syringes. They were sterilized by either irradiation or sterile filtration. They were injected subcutaneously in a total of 24 male beagle dogs. The dogs were then bled regularly at each time point to collect their plasma samples. The plasma samples were analyzed using a validated LC/MS/MS method by a contract analytical service company.

Test Articles for Example 5
TA 1: 20% buprenorphine free base in 40% 50/50 PLGH (26 kD) and 60% NMP, irradiated
TA 2: 20% buprenorphine free base in 40% 50/50 PLGH (12 kD) and 60% NMP, irradiated
TA 3: 20% buprenorphine free base in 40% 50/50 PLGH (21 kD) and 60% NMP, irradiated
TA 4: 20% buprenorphine free base in 40% 50/50 PLGH (21 kD) and 60% NMP, filtered

TABLE 6

Mean plasma buprenorphine levels after subcutaneous injection of four buprenorphine free base ATRIGEL ™ formulations in Beagles

| Time Points (Day) | TA 1 (ng/mL) | TA 2 (ng/mL) |
|---|---|---|
| Day 0 Hr 1 | 5.66 ± 2.64 | 10.25 ± 9.75 |
| Day 0 Hr 2 | 8.00 ± 4.14 | 14.33 ± 9.96 |
| Day 0 Hr 4 | 7.00 ± 3.04 | 11.93 ± 5.63 |
| Day 0 Hr 8 | 4.12 ± 1.66 | 7.00 ± 1.60 |
| 1 | 2.90 ± 1.23 | 5.99 ± 2.27 |
| 2 | 1.81 ± 0.68 | 3.82 ± 0.92 |
| 3 | 1.46 ± 0.62 | 2.71 ± 0.57 |
| 4 | 1.38 ± 0.52 | 2.39 ± 0.67 |
| 7 | 1.12 ± 0.46 | 2.37 ± 1.23 |
| 10 | 1.52 ± 0.60 | 2.65 ± 1.29 |
| 14 | 2.07 ± 1.15 | 3.55 ± 2.32 |
| 17 | 2.32 ± 1.24 | 3.64 ± 2.45 |
| 21 | 2.27 ± 1.11 | 2.36 ± 1.29 |
| 24 | 2.53 ± 1.60 | 2.21 ± 0.85 |
| 28 | 1.95 ± 1.04 | 1.41 ± 0.60 |
| 31 | 2.12 ± 1.17 | 1.28 ± 0.59 |
| 35 | 1.41 ± 0.52 | 0.98 ± 0.61 |
| 38 | 1.48 ± 0.76 | 0.91 ± 0.62 |
| 42 | 1.73 ± 0.97 | 0.90 ± 0.69 |
| 45 | 1.51 ± 0.83 | 0.89 ± 0.72 |
| 49 | 1.40 ± 0.57 | 0.68 ± 0.52 |
| 52 | 1.35 ± 0.71 | 0.79 ± 0.65 |
| 56 | 0.89 ± 0.34 | 0.64 ± 0.50 |
| 59 | 0.80 ± 0.30 | 0.59 ± 0.50 |
| 63 | 0.73 ± 0.28 | 0.56 ± 0.50 |
| 66 | 0.55 ± 0.18 | 0.59 ± 0.49 |
| 70 | 0.48 ± 0.17 | 0.49 ± 0.39 |
| 80 | 0.39 ± 0.19 | 0.46 ± 0.38 |
| 87 | 0.29 ± 0.20 | 0.44 ± 0.38 |
| 94 | 0.30 ± 0.27 | 0.46 ± 0.40 |
| 115 | 0.21 ± 0.22 | 0.22 ± 0.19 |
| 129 | 0.21 ± 0.22 | 0.27 ± 0.24 |
| 149 | 0.22 ± 0.21 | 0.26 ± 0.21 |

TABLE 6-continued

Mean plasma buprenorphine levels after subcutaneous injection of four buprenorphine free base ATRIGEL ™ formulations in Beagles

| | | |
|---|---|---|
| 176 | 0.10 ± 0.15 | 0.14 ± 0.13 |
| 192 | 0.09 ± 0.14 | 0.10 ± 0.12 |

| Time Points (Day) | TA 3 (ng/mL) | TA 4 (ng/mL) |
|---|---|---|
| Day 0 Hr 1 | 8.30 ± 3.43 | 6.08 ± 5.71 |
| Day 0 Hr 2 | 10.25 ± 3.22 | 8.40 ± 6.18 |
| Day 0 Hr 4 | 8.58 ± 2.99 | 7.03 ± 3.54 |
| Day 0 Hr 8 | 4.83 ± 1.46 | 4.32 ± 2.65 |
| 1 | 4.01 ± 1.03 | 2.58 ± 0.60 |
| 3 | 1.79 ± 0.33 | 1.43 ± 0.60 |
| 7 | 1.21 ± 0.35 | 0.85 ± 0.26 |
| 10 | 1.64 ± 0.60 | 1.15 ± 0.57 |
| 14 | 3.33 ± 1.02 | 2.23 ± 1.46 |
| 17 | 3.22 ± 0.90 | 2.07 ± 1.29 |
| 20 | 2.62 ± 0.88 | 1.63 ± 1.01 |
| 24 | 2.10 ± 0.71 | 1.16 ± 0.58 |
| 27 | 2.13 ± 0.80 | 1.18 ± 0.70 |
| 31 | 1.93 ± 0.65 | 1.18 ± 0.64 |
| 38 | 1.60 ± 0.44 | 1.06 ± 0.58 |
| 45 | 1.37 ± 0.58 | 1.10 ± 0.61 |
| 52 | 0.97 ± 0.63 | 0.99 ± 0.58 |
| 66 | 0.29 ± 0.23 | 0.57 ± 0.24 |
| 80 | 0.11 ± 0.13 | 0.26 ± 0.13 |
| 94 | 0.10 ± 0.15 | 0.20 ± 0.11 |
| 108 | 0.15 ± 0.28 | 0.20 ± 0.12 |
| 120 | 0.12 ± 0.20 | 0.17 ± 0.11 |
| 141 | 0.08 ± 0.14 | 0.13 ± 0.11 |
| 163 | 0.14 ± 0.28 | 0.12 ± 0.10 |
| 183 | 0.05 ± 0.08 | 0.12 ± 0.11 |

The invention claimed is:

1. An injectable flowable composition comprising:
   (i) 8 wt % to about 22 wt % of buprenorphine free base;
   (ii) about 25 wt % to about 50 wt % of a poly(DL-lactide-co-glycolide) biodegradable thermoplastic polymer; wherein the polymer has an average molecular weight of about 5,000 Daltons to about 40,000 Daltons; and
   (iii) about 30 wt % to about 70 wt % of N-methyl-2-pyrrolidone.

2. The composition of claim 1, wherein the composition is transformed in situ into a solid implant by contact with water or a bodily fluid.

3. The composition of claim 1, wherein the polymer is a 50/50 poly(DL-lactide-co-glycolide) biodegradable thermoplastic polymer.

4. The composition of claim 1, wherein the polymer has an average molecular weight of about 9,000 Daltons to about 20,000 Daltons.

5. The composition of claim 1, wherein the polymer has a carboxy terminal group.

6. The composition of claim 1, wherein the weight ratio of buprenorphine to polymer is between 0.01:1 and 2:1.

7. A method for treating a patient having an opioid dependency comprising parenterally administering to the patient a therapeutically effective amount of the composition of claim 1 once per month to treat the opioid dependency.

* * * * *